US008372959B2

(12) United States Patent
Jungbauer et al.

(10) Patent No.: US 8,372,959 B2
(45) Date of Patent: *Feb. 12, 2013

(54) PRODUCTION OF RECOMBINANT PROTEINS BY AUTOPROTEOLYTIC CLEAVAGE OF A FUSION PROTEIN

(75) Inventors: Alois Jungbauer, Vienna (AT); Rainer Hahn, Vienna (AT); Anne Tscheliessnig, Ledenitzen (AT); Waltraud Kaar, Indooroopilly (AU)

(73) Assignees: Sandoz AG, Basel (CH); Boehringer Ingelheim RCV GmbH & Co KG, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 13/348,607

(22) Filed: Jan. 11, 2012

(65) Prior Publication Data

US 2012/0107869 A1    May 3, 2012

Related U.S. Application Data

(62) Division of application No. 11/919,257, filed as application No. PCT/AT2006/000168 on Apr. 25, 2006, now Pat. No. 8,163,890.

(30) Foreign Application Priority Data

| Apr. 26, 2005 | (GB) | 0508434.8 |
| Apr. 26, 2005 | (GB) | 0508435.5 |
| Mar. 16, 2006 | (GB) | 0605379.7 |

(51) Int. Cl.

| A23J 1/00 | (2006.01) |
| C07K 17/00 | (2006.01) |
| C07K 16/00 | (2006.01) |
| C07K 14/00 | (2006.01) |
| C07K 1/00 | (2006.01) |
| C07K 5/00 | (2006.01) |
| C07K 7/00 | (2006.01) |
| A61K 38/04 | (2006.01) |

(52) U.S. Cl. ......... 530/412; 530/413; 530/328; 530/329
(58) Field of Classification Search .................. None
See application file for complete search history.

(56) References Cited

U.S. PATENT DOCUMENTS

| 6,936,455 B1 | 8/2005 | Stempfer et al. |
| 2003/0166240 A1 | 9/2003 | Shrader et al. |
| 2005/0036980 A1 | 2/2005 | Chaney et al. |

FOREIGN PATENT DOCUMENTS

| DE | 19819843 | 11/1999 |
| WO | WO-94/18345 A1 | 8/1994 |
| WO | WO-98/15572 A1 | 4/1998 |
| WO | WO-99/10483 A | 3/1999 |
| WO | WO-99/10483 A2 | 3/1999 |
| WO | WO-99/14232 A1 | 3/1999 |
| WO | WO-01/11056 A | 2/2001 |
| WO | WO-01/11056 A1 | 2/2001 |
| WO | WO-01/11057 A1 | 2/2001 |
| WO | WO-02/062969 A2 | 8/2002 |
| WO | WO-02/088171 A2 | 11/2002 |
| WO | WO-2004/043997 | 5/2004 |

OTHER PUBLICATIONS

Tillman et al., "N-terminal protease of pestiviruses: Identification of putative catalytic residues by site-directed mutagenesis," Journal of Virology, The American Society for Microbiology, vol. 72, No. 3, 1998, pp. 2544-2547, XP002156880, ISSN: 0022-538X.
Kool et al., "Functional analysis of the *Burkholderia cenocepacia* ZmpA metalloprotease," Journal of Bacteriology, vol. 187, No. 13, 2005, pp. 4421-4429, XP002412198, ISSN: 0021-9193.
Liu, Ruiwu et al., "Combinatorial peptide library methods for immunobiology research", Experimental Hematology, 2003, vol. 31, pp. 11-30.
Buettner, Joseph A. et al., "Chemically derived peptide libraries: A new resin and methodology for lead identification", Int. J. Protein Res., 1996, vol. 47, pp. 70-83.
Banki, Mahmoud Reza et al., "Novel and economical purification of recombinant proteins: Intein-mediated protein purification using in vivo polyhydroxybutyrate (PHB) matrix association," Protein Science, 2005, vol. 14, pp. 1387-1395.
Hong, Sung-Hye et al., "High yield expression and single step purification of human thionein/metallothionein," Protein Expression and Purification, 2001, vol. 23, p. 243-250.
Morassutti, Carla et al., "Expression of SMAP-29 cathelicidin-like peptide in bacterial cells by intein-mediated system," Protein Expression and Purification, 2005, vol. 39, pp. 160-168.
Written Opinion issued by the Intellectual Property Office of Singapore on May 23, 2011 in connection with corresponding Singapore Application No. 200717226-5.
Written Opinion and Search Report mailed by the Intellectual Property Office of Singapore on Aug. 4, 2010 in connection with corresponding Singapore Application No. 200717226-5.
Stark, Robert et al., "Processing of pestvirus polyprotein: Cleavage site between autoprotease and nucleocapsid protein of classical swine fever virus," Journal of Virology, Dec. 1993, vol. 67, No. 12, pp. 7088-7095. Office Action dated Aug. 2, 2011 in corresponding Japanese Patent Application No. 2008-508021 with English translation.
Alloza, I. et al., "Cross-linking approach to affinity capture of protein complexes from chaotrope-solubilized cell lysates," Analytical Biochemistry, Academic Press, San Diego, CA, US, vol. 324, No. 1, Jan. 1, 2004, pp. 137-142.
Davoodi-Semiromi A. et al., "Direct Submission," XP002397791, retrieved from NCBI Database accession No. AAL05891, 2002.
Ruemenapf, Tillman et al., "N-terminal protease of pestiviruses: Identification of putative catalytic residues by site-directed mutagenesis," Journal of Virology, the American Society for Microbiology, US, vol. 72, No. 3, Mar. 1, 1998, pp. 2544-2547.

*Primary Examiner* — Suzanne M Noakes
*Assistant Examiner* — Jae W Lee
(74) *Attorney, Agent, or Firm* — Birch, Stewart, Kolasch & Birch, LLP

(57) ABSTRACT

Disclosed is a method for the production of a heterologous polypeptide of interest with a homogenous N-terminus, using a fusion polypeptide comprising the polypeptide of interest and N-terminally thereto a polypeptide exhibiting autoproteolytic function, said method comprises the steps of a) binding of the fusion polypeptide in a soluble, autoproteolytically inactive form by an affinity chromatography system, b) refolding of the fusion polypeptide, thereby activating the autoproteolytic function of the fusion polypeptide and causing cleavage of the heterologous polypeptide of interest, and c) subsequently eluting the heterologous polypeptide of interest, wherein the steps are conducted on one affinity chromatography system.

18 Claims, No Drawings

SEQUENCE LISTING

```
<160> NUMBER OF SEQ ID NOS: 208

<210> SEQ ID NO 1
<211> LENGTH: 168
<212> TYPE: PRT
<213> ORGANISM: Pestivirus

<400> SEQUENCE: 1

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 2
<211> LENGTH: 168
<212> TYPE: PRT
<213> ORGANISM: Artificial Sequence
<220> FEATURE:
<223> OTHER INFORMATION: Synthetic modified N-protease of Pestivirus

<400> SEQUENCE: 2

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80
```

```
Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 3
<211> LENGTH: 168
<212> TYPE: PRT
<213> ORGANISM: Artificial Sequence
<220> FEATURE:
<223> OTHER INFORMATION: Synthetic modified N-protease of Pestivirus

<400> SEQUENCE: 3

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 4
<211> LENGTH: 168
<212> TYPE: PRT
<213> ORGANISM: Artificial Sequence
<220> FEATURE:
<223> OTHER INFORMATION: Synthetic modified N-protease of Pestivirus

<400> SEQUENCE: 4

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45
```

```
His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Leu Ala
            130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165

<210> SEQ ID NO 5
<211> LENGTH: 168
<212> TYPE: PRT
<213> ORGANISM: Artificial Sequence
<220> FEATURE:
<223> OTHER INFORMATION: Synthetic modified N-protease of Pestivirus

<400> SEQUENCE: 5

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Gln Ala
            130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165

<210> SEQ ID NO 6
<211> LENGTH: 6
<212> TYPE: PRT
<213> ORGANISM: Pestivirus

<400> SEQUENCE: 6

Val Ser Ile Phe Glu Trp
1               5
```

```
<210> SEQ ID NO 7
<211> LENGTH: 7
<212> TYPE: PRT
<213> ORGANISM: Pestivirus

<400> SEQUENCE: 7

Ala Val Ser Ile Glu Trp Tyr
1               5

<210> SEQ ID NO 8
<211> LENGTH: 7
<212> TYPE: PRT
<213> ORGANISM: Pestivirus

<400> SEQUENCE: 8

Ala Val Ser Phe Ile Trp Tyr
1               5

<210> SEQ ID NO 9
<211> LENGTH: 7
<212> TYPE: PRT
<213> ORGANISM: Pestivirus

<400> SEQUENCE: 9

Val Ser Phe Ile Trp Tyr Lys
1               5

<210> SEQ ID NO 10
<211> LENGTH: 7
<212> TYPE: PRT
<213> ORGANISM: Pestivirus

<400> SEQUENCE: 10

Ala Ser Arg Phe Trp Tyr Ala
1               5

<210> SEQ ID NO 11
<211> LENGTH: 7
<212> TYPE: PRT
<213> ORGANISM: Pestivirus

<400> SEQUENCE: 11

Ala Phe Tyr Thr Trp Tyr Ala
1               5

<210> SEQ ID NO 12
<211> LENGTH: 7
<212> TYPE: PRT
<213> ORGANISM: Pestivirus

<400> SEQUENCE: 12

Ala Phe Tyr Arg Trp Tyr Lys
1               5

<210> SEQ ID NO 13
<211> LENGTH: 6
<212> TYPE: PRT
<213> ORGANISM: Pestivirus

<400> SEQUENCE: 13

Ala Phe Tyr Arg Trp Tyr
1               5

<210> SEQ ID NO 14
<211> LENGTH: 7
<212> TYPE: PRT
```

```
<213> ORGANISM: Pestivirus

<400> SEQUENCE: 14

Ala Phe Tyr Arg Trp Tyr Ala
1               5

<210> SEQ ID NO 15
<211> LENGTH: 8
<212> TYPE: PRT
<213> ORGANISM: Pestivirus

<400> SEQUENCE: 15

Ala Val Ser Ile Phe Glu Trp Tyr
1               5

<210> SEQ ID NO 16
<211> LENGTH: 7
<212> TYPE: PRT
<213> ORGANISM: Pestivirus

<400> SEQUENCE: 16

Ala Val Ser Arg Asn Trp Tyr
1               5

<210> SEQ ID NO 17
<211> LENGTH: 6
<212> TYPE: PRT
<213> ORGANISM: Pestivirus

<400> SEQUENCE: 17

Ala Ser Arg Phe Trp Tyr
1               5

<210> SEQ ID NO 18
<211> LENGTH: 8
<212> TYPE: PRT
<213> ORGANISM: Pestivirus

<400> SEQUENCE: 18

Ala Phe Tyr Arg Trp Tyr Ala Ala
1               5

<210> SEQ ID NO 19
<211> LENGTH: 6
<212> TYPE: PRT
<213> ORGANISM: Pestivirus

<400> SEQUENCE: 19

Ala Phe Tyr Arg Trp Tyr
1               5

<210> SEQ ID NO 20
<211> LENGTH: 8
<212> TYPE: PRT
<213> ORGANISM: Pestivirus

<400> SEQUENCE: 20

Ala Ser Arg Phe Trp Tyr Ala Ala
1               5

<210> SEQ ID NO 21
<211> LENGTH: 8
<212> TYPE: PRT
<213> ORGANISM: Pestivirus

<400> SEQUENCE: 21
```

```
Ala Phe Tyr Arg Trp Tyr Ala Ala
1               5

<210> SEQ ID NO 22
<211> LENGTH: 8
<212> TYPE: PRT
<213> ORGANISM: Pestivirus

<400> SEQUENCE: 22

Ala Phe Tyr Ser Trp Tyr Ala Ala
1               5

<210> SEQ ID NO 23
<211> LENGTH: 415
<212> TYPE: PRT
<213> ORGANISM: Pestivirus

<400> SEQUENCE: 23

Met His His His His His His Glu Leu Asn His Phe Glu Leu Leu Tyr
1               5                   10                  15

Lys Thr Ser Lys Gln Lys Pro Val Gly Val Glu Glu Pro Val Tyr Asp
            20                  25                  30

Thr Ala Gly Arg Pro Leu Phe Gly Asn Pro Ser Glu Val His Pro Gln
        35                  40                  45

Ser Thr Leu Lys Leu Pro His Asp Arg Gly Arg Gly Asp Ile Arg Thr
    50                  55                  60

Thr Leu Arg Asp Leu Pro Arg Lys Gly Asp Cys Arg Ser Gly Asn His
65                  70                  75                  80

Leu Gly Pro Val Ser Gly Ile Tyr Ile Lys Pro Gly Pro Val Tyr Tyr
                85                  90                  95

Gln Asp Tyr Thr Gly Pro Val Tyr His Arg Ala Pro Leu Glu Phe Phe
            100                 105                 110

Asp Glu Ala Gln Phe Cys Glu Val Thr Lys Arg Ile Gly Arg Val Thr
        115                 120                 125

Gly Ser Asp Gly Lys Leu Tyr His Ile Tyr Val Cys Val Asp Gly Cys
    130                 135                 140

Ile Leu Leu Lys Leu Ala Lys Arg Gly Thr Pro Arg Thr Leu Lys Trp
145                 150                 155                 160

Ile Arg Asn Phe Thr Asn Cys Pro Leu Trp Val Thr Ser Cys Ser Gly
                165                 170                 175

Thr Met Arg Lys Gly Glu Glu Leu Phe Thr Gly Val Val Pro Ile Leu
            180                 185                 190

Val Glu Leu Asp Gly Asp Val Asn Gly His Lys Phe Ser Val Ser Gly
        195                 200                 205

Glu Gly Glu Gly Asp Ala Thr Tyr Gly Lys Leu Thr Leu Lys Phe Ile
    210                 215                 220

Cys Thr Thr Gly Lys Leu Pro Val Pro Trp Pro Thr Leu Val Thr Thr
225                 230                 235                 240

Phe Gly Tyr Gly Val Gln Cys Phe Ala Arg Tyr Pro Asp His Met Lys
                245                 250                 255

Gln His Asp Phe Phe Lys Ser Ala Met Pro Glu Gly Tyr Val Gln Glu
            260                 265                 270

Arg Thr Ile Phe Phe Lys Asp Asp Gly Asn Tyr Lys Thr Arg Ala Glu
        275                 280                 285

Val Lys Phe Glu Gly Asp Thr Leu Val Asn Arg Ile Glu Leu Lys Gly
    290                 295                 300
```

```
Ile Asp Phe Lys Glu Asp Gly Asn Ile Leu Gly His Lys Leu Glu Tyr
305                 310                 315                 320

Asn Tyr Asn Ser His Asn Val Tyr Ile Met Ala Asp Lys Gln Lys Asn
            325                 330                 335

Gly Ile Lys Val Asn Phe Lys Ile Arg His Asn Ile Glu Asp Gly Ser
        340                 345                 350

Val Gln Leu Ala Asp His Tyr Gln Gln Asn Thr Pro Ile Gly Asp Gly
    355                 360                 365

Pro Val Leu Leu Pro Asp Asn His Tyr Leu Ser Thr Gln Ser Ala Leu
370                 375                 380

Ser Lys Asp Pro Asn Glu Lys Arg Asp His Met Val Leu Leu Glu Phe
385                 390                 395                 400

Val Thr Ala Ala Gly Ile Thr His Gly Met Asp Glu Leu Tyr Lys
                405                 410                 415

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
gaaattaata cgactcacta tagg                                          24

<210> SEQ ID NO 25
<211> LENGTH: 30
<212> TYPE: DNA
<213> ORGANISM: Artificial Sequence
<220> FEATURE:
<223> OTHER INFORMATION: Synthetic primer

<400> SEQUENCE: 25
cggtaccaga gcaactagtt acccataatg                                    30

<210> SEQ ID NO 26
<211> LENGTH: 26
<212> TYPE: DNA
<213> ORGANISM: Artificial Sequence
<220> FEATURE:
<223> OTHER INFORMATION: Synthetic primer

<400> SEQUENCE: 26
gaaaggtacc atgcgtaaag gagaag                                        26

<210> SEQ ID NO 27
<211> LENGTH: 33
<212> TYPE: DNA
<213> ORGANISM: Artificial Sequence
<220> FEATURE:
<223> OTHER INFORMATION: Synthetic primer

<400> SEQUENCE: 27
taagtcgact tatttgtata gttcatccat gcc                                33

<210> SEQ ID NO 28
<211> LENGTH: 768
<212> TYPE: DNA
<213> ORGANISM: Artificial Sequence
<220> FEATURE:
<223> OTHER INFORMATION: Synthetic plasmid

<400> SEQUENCE: 28
atggaactca atcatttcga actgctctac aaaactagca agcaaaaacc tgttggcgtt   60
```

```
gaagagccgg tctacgatac tgcaggtcgt cctcttttg  ggaatccgtc cgaagtgcac      120
ccccagtcaa ccctcaagct tccccatgac cgcggacgcg gtgacattcg tacaacgctg      180
cgcgatctgc ctcgtaaagg cgattgtcgc tctggaaacc acctaggtcc ggtgtcgggc      240
atttacatta aaccaggtcc cgtctattac caagactaca ctggtccggt ttaccatcgt      300
gcacctctgg aattctttga tgaagctcaa ttttgcgaag tgactaaacg tattggccgt      360
gtaaccggtt cggacgggaa actgtaccac atctacgtgt gcgttgatgg ctgtatcctg      420
ctgaaactcg cgaagcgcgg aaccctcgc  accctgaaat ggatccgtaa cttcactaac      480
tgtccactgt gggtcactag ttgcttcgtt aaccaacatc tgtgcggttc acaccttgtg      540
gaagccctgt atctggtgtg tggcgaacgc ggattctttt ataccccgaa aacgcggcgc      600
gaagccgaag atcttcaggt tggtcaagtg gaactgggcg gaggtccggg agccgggagc      660
ctgcaaccgc tggcgcttga agggtcgctg caaaaacgcg gtattgttga acagtgctgt      720
acctccatct gctctctgta tcagctggaa aactactgca attaataa                   768
```

<210> SEQ ID NO 29
<211> LENGTH: 52
<212> TYPE: DNA
<213> ORGANISM: Artificial Sequence
<220> FEATURE:
<223> OTHER INFORMATION: Synthetic primer

<400> SEQUENCE: 29

```
ctctcatatg catcaccatc atcatcacga actcaatcat ttcgaactgc tc              52
```

<210> SEQ ID NO 30
<211> LENGTH: 32
<212> TYPE: DNA
<213> ORGANISM: Artificial Sequence
<220> FEATURE:
<223> OTHER INFORMATION: Synthetic primer

<400> SEQUENCE: 30

```
ctttcgtcga cttattaatt gcagtagttt tc                                    32
```

<210> SEQ ID NO 31
<211> LENGTH: 30
<212> TYPE: DNA
<213> ORGANISM: Artificial Sequence
<220> FEATURE:
<223> OTHER INFORMATION: Synthetic primer

<400> SEQUENCE: 31

```
cgcgacatat ggaactcaat catttcgaac                                       30
```

<210> SEQ ID NO 32
<211> LENGTH: 32
<212> TYPE: DNA
<213> ORGANISM: Artificial Sequence
<220> FEATURE:
<223> OTHER INFORMATION: Synthetic primer

<400> SEQUENCE: 32

```
cgcagagatg ttggtcgacg ctgcaactag tg                                    32
```

<210> SEQ ID NO 33
<211> LENGTH: 52
<212> TYPE: DNA
<213> ORGANISM: Artificial Sequence
<220> FEATURE:
<223> OTHER INFORMATION: Synthetic primer

<400> SEQUENCE: 33
gcaactagtg acccacagtg gacagttagt ggtgttacgg gtccatttca gg    52

<210> SEQ ID NO 34
<211> LENGTH: 26
<212> TYPE: DNA
<213> ORGANISM: Artificial Sequence
<220> FEATURE:
<223> OTHER INFORMATION: Synthetic plasmid

<400> SEQUENCE: 34
gctcaatttg aggaagtgac taaacg    26

<210> SEQ ID NO 35
<211> LENGTH: 26
<212> TYPE: DNA
<213> ORGANISM: Artificial Sequence
<220> FEATURE:
<223> OTHER INFORMATION: Synthetic plasmid

<400> SEQUENCE: 35
cgtttagtca cttcctcaaa ttgagc    26

<210> SEQ ID NO 36
<211> LENGTH: 22
<212> TYPE: DNA
<213> ORGANISM: Artificial Sequence
<220> FEATURE:
<223> OTHER INFORMATION: Synthetic plasmid

<400> SEQUENCE: 36
catctacgtg gaggttgatg gc    22

<210> SEQ ID NO 37
<211> LENGTH: 22
<212> TYPE: DNA
<213> ORGANISM: Artificial Sequence
<220> FEATURE:
<223> OTHER INFORMATION: Synthetic plasmid

<400> SEQUENCE: 37
gccatcaacc tccacgtaga tg    22

<210> SEQ ID NO 38
<211> LENGTH: 21
<212> TYPE: DNA
<213> ORGANISM: Artificial Sequence
<220> FEATURE:
<223> OTHER INFORMATION: Synthetic plasmid

<400> SEQUENCE: 38
gttgatggcg agatcctgct g    21

<210> SEQ ID NO 39
<211> LENGTH: 21
<212> TYPE: DNA
<213> ORGANISM: Artificial Sequence
<220> FEATURE:
<223> OTHER INFORMATION: Synthetic plasmid

<400> SEQUENCE: 39
cagcaggatc tcgccatcaa c    21

<210> SEQ ID NO 40
<211> LENGTH: 50

```
<212> TYPE: DNA
<213> ORGANISM: Artificial Sequence
<220> FEATURE:
<223> OTHER INFORMATION: Synthetic plasmid

<400> SEQUENCE: 40
ctggaattct ttgatgaaac ccaatttgag gaaaccacta aacgtattgg          50

<210> SEQ ID NO 41
<211> LENGTH: 50
<212> TYPE: DNA
<213> ORGANISM: Artificial Sequence
<220> FEATURE:
<223> OTHER INFORMATION: Synthetic plasmid

<400> SEQUENCE: 41
ccaatacgtt tagtggtttc ctcaaattgg gtttcatcaa agaattccag          50

<210> SEQ ID NO 42
<211> LENGTH: 37
<212> TYPE: DNA
<213> ORGANISM: Artificial Sequence
<220> FEATURE:
<223> OTHER INFORMATION: Synthetic plasmid

<400> SEQUENCE: 42
catgaccgcg gagaagatga cattgaaaca acgctgc                       37

<210> SEQ ID NO 43
<211> LENGTH: 38
<212> TYPE: DNA
<213> ORGANISM: Artificial Sequence
<220> FEATURE:
<223> OTHER INFORMATION: Synthetic plasmid

<400> SEQUENCE: 43
gcagcgttgt ttcaatgttc accttctccg cggtcatg                      38

<210> SEQ ID NO 44
<211> LENGTH: 30
<212> TYPE: DNA
<213> ORGANISM: Artificial Sequence
<220> FEATURE:
<223> OTHER INFORMATION: Synthetic plasmid

<400> SEQUENCE: 44
gatcctgctg aaacaggcga agcgcggaac                               30

<210> SEQ ID NO 45
<211> LENGTH: 30
<212> TYPE: DNA
<213> ORGANISM: Artificial Sequence
<220> FEATURE:
<223> OTHER INFORMATION: Synthetic plasmid

<400> SEQUENCE: 45
gttccgcgct tcgcctgttt cagcaggatc                               30

<210> SEQ ID NO 46
<211> LENGTH: 720
<212> TYPE: DNA
<213> ORGANISM: Artificial Sequence
<220> FEATURE:
<223> OTHER INFORMATION: Synthetic plasmid

<400> SEQUENCE: 46
tgcagcaaag gcgaagaact gtttaccggt gtggtgccga ttctggtgga actggatggc   60
```

-continued

```
gatgtgaacg gtcataaatt tagcgtgagc ggcgaaggtg aaggcgatgc gacctatggt    120
aaactgaccc tgaaatttat ttgcaccacc ggcaaactgc cggtgccgtg ccgaccctg     180 gtgaccacct ttggttatgg cgtgcagtgc tttgcgcgct atccggatca catgaaacag    240
catgattttt ttaaaagcgc gatgccggaa ggttatgtgc aggaacgcac cattttttt     300 aaagatgatg caactataa aacccgcgcg aagtgaaat ttgaaggtga taccctggtg     360
aaccgcattg aactgaaagg cattgatttt aaagaagatg gtaacattct gggccataaa    420
ctggaatata actataacag ccataacgtg tatattatgg cggataaaca gaaaaacggt    480
attaaagtga actttaaaat tcgccataac attgaagatg gcagcgtgca gctggcggat    540
cattatcagc agaacacccc gattggtgat ggcccggtgc tgctgccgga taaccattat    600
ctgagcaccc agagcgcgct gagcaaagat ccgaacgaaa aacgcgatca catggtgctg    660
ctggaatttg tgaccgcggc gggtattacg catggcatgg atgaactgta taataataa    720
```

<210> SEQ ID NO 47
<211> LENGTH: 28
<212> TYPE: DNA
<213> ORGANISM: Artificial Sequence
<220> FEATURE:
<223> OTHER INFORMATION: Synthetic primer

<400> SEQUENCE: 47

```
ggatccacta gttgcagcaa aggcgaag                                        28
```

<210> SEQ ID NO 48
<211> LENGTH: 31
<212> TYPE: DNA
<213> ORGANISM: Artificial Sequence
<220> FEATURE:
<223> OTHER INFORMATION: Synthetic primer

<400> SEQUENCE: 48

```
cgaggtcgac ttattattta tacagttcat c                                    31
```

<210> SEQ ID NO 49
<211> LENGTH: 411
<212> TYPE: PRT
<213> ORGANISM: Artificial Sequence
<220> FEATURE:
<223> OTHER INFORMATION: Synthetic autoprotease

<400> SEQUENCE: 49

```
Met His His His His His His Glu Leu Asn His Phe Glu Leu Leu Tyr
1               5                   10                  15

Lys Thr Ser Lys Gln Lys Pro Val Gly Val Glu Glu Pro Val Tyr Asp
            20                  25                  30

Thr Ala Gly Arg Pro Leu Phe Gly Asn Pro Ser Glu Val His Pro Gln
        35                  40                  45

Ser Thr Leu Lys Leu Pro His Asp Arg Gly Glu Asp Ile Glu Thr
    50                  55                  60

Thr Leu Arg Asp Leu Pro Arg Lys Gly Asp Cys Arg Ser Gly Asn His
65                  70                  75                  80

Leu Gly Pro Val Ser Gly Ile Tyr Ile Lys Pro Gly Pro Val Tyr Tyr
                85                  90                  95

Gln Asp Tyr Thr Gly Pro Val Tyr His Arg Ala Pro Leu Glu Phe Phe
            100                 105                 110

Asp Glu Thr Gln Phe Glu Glu Thr Thr Lys Arg Ile Gly Arg Val Thr
        115                 120                 125
```

```
Gly Ser Asp Gly Lys Leu Tyr His Ile Tyr Val Glu Val Asp Gly Glu
            130                 135                 140

Ile Leu Leu Lys Gln Ala Lys Arg Gly Thr Pro Arg Thr Leu Lys Trp
145                 150                 155                 160

Thr Arg Asn Thr Thr Asn Cys Pro Leu Trp Val Thr Ser Cys Ser Lys
                165                 170                 175

Gly Glu Glu Leu Phe Thr Gly Val Val Pro Ile Leu Val Glu Leu Asp
            180                 185                 190

Gly Asp Val Asn Gly His Lys Phe Ser Val Ser Gly Glu Gly Glu Gly
            195                 200                 205

Asp Ala Thr Tyr Gly Lys Leu Thr Leu Lys Phe Ile Cys Thr Thr Gly
            210                 215                 220

Lys Leu Pro Val Pro Trp Pro Thr Leu Val Thr Thr Phe Gly Tyr Gly
225                 230                 235                 240

Val Gln Cys Phe Ala Arg Tyr Pro Asp His Met Lys Gln His Asp Phe
                245                 250                 255

Phe Lys Ser Ala Met Pro Glu Gly Tyr Val Gln Glu Arg Thr Ile Phe
            260                 265                 270

Phe Lys Asp Asp Gly Asn Tyr Lys Thr Arg Ala Glu Val Lys Phe Glu
            275                 280                 285

Gly Asp Thr Leu Val Asn Arg Ile Glu Leu Lys Gly Ile Asp Phe Lys
290                 295                 300

Glu Asp Gly Asn Ile Leu Gly His Lys Leu Glu Tyr Asn Tyr Asn Ser
305                 310                 315                 320

His Asn Val Tyr Ile Met Ala Asp Lys Gln Lys Asn Gly Ile Lys Val
                325                 330                 335

Asn Phe Lys Ile Arg His Asn Ile Glu Asp Gly Ser Val Gln Leu Ala
            340                 345                 350

Asp His Tyr Gln Gln Asn Thr Pro Ile Gly Asp Gly Pro Val Leu Leu
            355                 360                 365

Pro Asp Asn His Tyr Leu Ser Thr Gln Ser Ala Leu Ser Lys Asp Pro
370                 375                 380

Asn Glu Lys Arg Asp His Met Val Leu Leu Glu Phe Val Thr Ala Ala
385                 390                 395                 400

Gly Ile Thr His Gly Met Asp Glu Leu Tyr Lys
                405                 410

<210> SEQ ID NO 50
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 50

Met Glu Leu Asn His Phe Glu Leu Leu Tyr Lys Thr Ser Lys Gln Lys
1               5                   10                  15

Pro Val Gly Val Glu Glu Pro Tyr Asp Thr Ala Gly Arg Pro Leu
            20                  25                  30

Phe Gly Thr Pro Ser Glu Val His Pro Gln Ser Thr Leu Lys Leu Pro
            35                  40                  45

His Asp Arg Gly Glu Asp Ile Glu Thr Thr Leu Arg Asp Leu Pro
            50                  55                  60

Arg Lys Gly Asp Cys Arg Ser Gly Asn His Leu Gly Pro Val Ser Gly
65                  70                  75                  80
```

```
Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Ser Thr Asn
145                 150                 155                 160

Cys Pro Leu Trp Val Thr Ser Cys
                165

<210> SEQ ID NO 51
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 51

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Glu Gly Arg Pro Leu
            20                  25                  30

Phe Gly Thr Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Phe Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro His Thr Leu Lys Trp Thr Arg Asn Ser Thr Asn
145                 150                 155                 160

Cys Pro Leu Trp Val Thr Ser Cys
                165

<210> SEQ ID NO 52
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 52

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45
```

```
His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Ser Ala
    130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 53
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 53

Met Glu Leu Asn His Phe Glu Leu Leu Tyr Lys Thr Ser Lys Gln Lys
1               5                   10                  15

Pro Val Gly Val Glu Pro Val Tyr Asp Thr Ala Gly Arg Pro Leu
            20                  25                  30

Phe Gly Asn Pro Ser Glu Val His Pro Gln Ser Thr Leu Lys Leu Pro
            35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Asn Ala
    130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 54
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 54

Met Glu Leu Asn His Phe Glu Leu Leu Tyr Lys Thr Ser Lys Gln Lys
1               5                   10                  15
```

```
Pro Val Gly Val Glu Glu Pro Val Tyr Asp Thr Ala Gly Arg Pro Leu
             20                  25                  30

Phe Gly Asn Pro Ser Glu Val His Pro Gln Ser Thr Leu Lys Leu Pro
         35                  40                  45

His Asp Arg Gly Glu Asp Ile Glu Thr Thr Leu Arg Asp Leu Pro
 50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ser Gln Phe Glu
                100                 105                 110

Glu Ser Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Asp Ala
        130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 55
<211> LENGTH: 168
<212> TYPE: PRT
<213> ORGANISM: Artificial Sequence
<220> FEATURE:
<223> OTHER INFORMATION: Synthetic derivative of seq id no 1

<400> SEQUENCE: 55

Met Glu Leu Asn His Phe Glu Leu Leu Tyr Lys Thr Ser Lys Gln Lys
 1               5                  10                  15

Pro Val Gly Val Glu Glu Pro Val Tyr Asp Thr Ala Gly Arg Pro Leu
             20                  25                  30

Phe Gly Asn Pro Ser Glu Val His Pro Gln Ser Thr Leu Lys Leu Pro
         35                  40                  45

His Asp Arg Gly Glu Asp Ile Glu Thr Thr Leu Arg Asp Leu Pro
 50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ser Gln Phe Glu
                100                 105                 110

Glu Ser Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys His Ala
        130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 56
<211> LENGTH: 168
<212> TYPE: PRT
<213> ORGANISM: Artificial Sequence
<220> FEATURE:
<223> OTHER INFORMATION: Synthetic derivative of seq id no 1
```

```
<400> SEQUENCE: 56

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Cys Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

Glu Asp Asp Ile Glu
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide

<400> SEQUENCE: 58

Arg Gly Asp Ile Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide

<400> SEQUENCE: 59

Val Ser Asp Asp Trp Tyr
1               5

<210> SEQ ID NO 60
<211> LENGTH: 6
<212> TYPE: PRT
<213> ORGANISM: Artificial Sequence
```

<220> FEATURE:
<223> OTHER INFORMATION: Synthetic peptide

<400> SEQUENCE: 60

Val Ser Glu Asp Trp Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide

<400> SEQUENCE: 61

Val Ser Ile Asp Trp Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide

<400> SEQUENCE: 62

Val Ser Tyr Asp Trp Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide

<400> SEQUENCE: 63

Val Ser Val Asp Trp Tyr
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide

<400> SEQUENCE: 64

Val Ser Trp Asp Trp Tyr
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic peptide

<400> SEQUENCE: 65

Val Ser Tyr Asp Trp Tyr
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 66

Val Ser Phe Asp Trp Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Val Ser Asp Glu Trp Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide

<400> SEQUENCE: 68

Val Ser Glu Glu Trp Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide

<400> SEQUENCE: 69

Val Ser Ile Glu Trp Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic peptide

<400> SEQUENCE: 70

Val Ser Tyr Glu Trp Tyr
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide

<400> SEQUENCE: 71

Val Ser Val Glu Trp Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide

<400> SEQUENCE: 72
```

```
Val Ser Trp Glu Trp Tyr
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide

<400> SEQUENCE: 73

Val Ser Tyr Glu Trp Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide

<400> SEQUENCE: 74

Val Ser Phe Glu Trp Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide

<400> SEQUENCE: 75

Asp Asp Asp Asp Trp Tyr
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide

<400> SEQUENCE: 76

Asp Asp Glu Asp Trp Tyr
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic peptide

<400> SEQUENCE: 77

Asp Asp Ile Asp Trp Tyr
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic peptide

<400> SEQUENCE: 78

Asp Asp Tyr Asp Trp Tyr
```

<210> SEQ ID NO 79
<211> LENGTH: 6
<212> TYPE: PRT
<213> ORGANISM: Artificial Sequence
<220> FEATURE:
<223> OTHER INFORMATION: Synthetic peptide

<400> SEQUENCE: 79

Asp Asp Val Asp Trp Tyr
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic peptide

<400> SEQUENCE: 80

Asp Asp Trp Asp Trp Tyr
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic peptide

<400> SEQUENCE: 81

Asp Asp Tyr Asp Trp Tyr
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide

<400> SEQUENCE: 82

Asp Asp Phe Asp Trp Tyr
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide

<400> SEQUENCE: 83

Val Ser Ile Phe Trp Glu
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic peptide

<400> SEQUENCE: 84

Phe Ser Ile Phe Glu Trp
1               5

```
<210> SEQ ID NO 85
<211> LENGTH: 6
<212> TYPE: PRT
<213> ORGANISM: Artificial Sequence
<220> FEATURE:
<223> OTHER INFORMATION: Synthetic peptide

<400> SEQUENCE: 85

Trp Ser Ile Phe Glu Trp
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide

<400> SEQUENCE: 86

Val Ser Leu Ile Trp Tyr
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic peptide

<400> SEQUENCE: 87

Val Ser Leu Ile Asp Trp
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88

Val Ser Leu Ile Glu Trp
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic peptide

<400> SEQUENCE: 89

Val Ser Leu Ile Trp Glu
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic peptide

<400> SEQUENCE: 90

Phe Ser Leu Glu Glu Trp
1               5

<210> SEQ ID NO 91
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 91

Val Ser Asp Leu Asp Trp
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic peptide

<400> SEQUENCE: 92

Val Ser Asp Leu Glu Trp
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic peptide

<400> SEQUENCE: 93

Val Ser Tyr Ile Asp Trp
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic peptide

<400> SEQUENCE: 94

Val Ser Tyr Ile Trp Glu
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic peptide

<400> SEQUENCE: 95

Val Ser Ile Asp Trp Tyr
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic peptide

<400> SEQUENCE: 96

Val Ser Ile Glu Trp Tyr
1               5

<210> SEQ ID NO 97
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 97

Val Ser Ile Trp Trp Tyr
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide

<400> SEQUENCE: 98

Val Ser Ile Ile Trp Tyr
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide

<400> SEQUENCE: 99

Val Ser Tyr Ile Trp Tyr
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic peptide

<400> SEQUENCE: 100

Val Ser Val Ile Trp Tyr
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic peptide

<400> SEQUENCE: 101

Val Ser Phe Ile Trp Tyr
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic peptide

<400> SEQUENCE: 102

Val Ser Phe Ile Trp Glu
1               5

<210> SEQ ID NO 103
<211> LENGTH: 6
<212> TYPE: PRT
<213> ORGANISM: Artificial Sequence
<220> FEATURE:
```

<223> OTHER INFORMATION: Synthetic peptide

<400> SEQUENCE: 103

Val Ser Ile Phe Trp Glu
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic peptide

<400> SEQUENCE: 104

Phe Ser Ile Phe Glu Trp
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic peptide

<400> SEQUENCE: 105

Trp Ser Ile Phe Glu Trp
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic peptide

<400> SEQUENCE: 106

Val Ser Leu Ile Trp Tyr
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic peptide

<400> SEQUENCE: 107

Val Ser Leu Ile Asp Trp
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic peptide

<400> SEQUENCE: 108

Val Ser Leu Ile Glu Trp
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 109

Val Ser Leu Ile Trp Glu
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic peptide

<400> SEQUENCE: 110

Phe Ser Leu Ile Glu Trp
1               5

<210> SEQ ID NO 111
<211> LENGTH: 6
<212> TYPE: PRT
<213> ORGANISM: Artificial Sequence
<220> FEATURE:
<223> OTHER INFORMATION: Synthetic peptide

<400> SEQUENCE: 111

Trp Ser Leu Ile Glu Trp
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic peptide

<400> SEQUENCE: 112

Phe Ser Tyr Phe Glu Trp
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic peptide

<400> SEQUENCE: 113

Phe Ser Phe Tyr Glu Trp
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic peptide

<400> SEQUENCE: 114

Trp Ser Phe Tyr Glu Trp
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic peptide

<400> SEQUENCE: 115
```

```
Phe Ser Tyr Ile Glu Trp
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic peptide

<400> SEQUENCE: 116

Trp Ser Tyr Ile Glu Trp
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide

<400> SEQUENCE: 117

Ala Phe Phe Arg Trp Tyr Ala
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 118

Ala Phe Gly Arg Trp Tyr Ala
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Ala Phe His Arg Trp Tyr Ala
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

Ala Phe Ile Arg Trp Tyr Ala
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 121

Ala Phe Leu Arg Trp Tyr Ala
1               5
```

```
<210> SEQ ID NO 122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 122

Ala Phe Thr Arg Trp Tyr Ala
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide

<400> SEQUENCE: 123

Ala Phe Val Arg Trp Tyr Ala
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 124

Ala Phe Tyr Phe Trp Tyr Ala
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide

<400> SEQUENCE: 125

Ala Phe Tyr Gly Trp Tyr Ala
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic peptide

<400> SEQUENCE: 126

Ala Phe Tyr Leu Trp Tyr Ala
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 127

Ala Phe Tyr Met Trp Tyr Ala
1               5
```

```
<210> SEQ ID NO 128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Ala Phe Tyr Asn Trp Tyr Ala
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 129

Ala Phe Tyr Pro Trp Tyr Ala
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 130

Ala Phe Tyr Val Trp Tyr Ala
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 131

Ala Phe Tyr Trp Trp Tyr Ala
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132

Ala Phe Tyr Tyr Trp Tyr Ala
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide

<400> SEQUENCE: 133

Ala Lys Trp Phe Arg Tyr Ala
1               5

<210> SEQ ID NO 134
<211> LENGTH: 6
```

```
<212> TYPE: PRT
<213> ORGANISM: Artificial Sequence
<220> FEATURE:
<223> OTHER INFORMATION: Synthetic peptide

<400> SEQUENCE: 134

Val Ser Arg Asn Trp Tyr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic peptide

<400> SEQUENCE: 135

Ala Ser Arg Asn Trp Tyr Ala
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 136

Phe Ser Arg Asn Trp Tyr Ala
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic peptide

<400> SEQUENCE: 137

Val Phe Arg Asn Trp Tyr Ala
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic peptide

<400> SEQUENCE: 138

Val Trp Arg Asn Trp Tyr Ala
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic peptide

<400> SEQUENCE: 139

Val Tyr Arg Asn Trp Tyr Ala
1               5

<210> SEQ ID NO 140
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 140

Val Ser Arg Ala Trp Tyr Ala
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic peptide

<400> SEQUENCE: 141

Val Ser Arg Phe Trp Tyr Ala
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide

<400> SEQUENCE: 142

Val Ser Arg Trp Trp Tyr Ala
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic peptide

<400> SEQUENCE: 143

Val Ser Arg Tyr Trp Tyr Ala
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide

<400> SEQUENCE: 144

Val Ser Arg Asn Phe Tyr Ala
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide

<400> SEQUENCE: 145

Val Ser Arg Asn Tyr Tyr Ala
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 146

Val Ser Arg Asn Trp Phe Ala
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 147

Val Ser Arg Asn Trp Trp Ala
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 148

Ala Phe Tyr Thr Trp Tyr Ala Lys
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 149

Ala Phe Tyr Arg Trp Tyr Lys Lys
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 150

Ala Phe Tyr Arg Trp Tyr Lys
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

<223> OTHER INFORMATION: ACETYLATION

<400> SEQUENCE: 151

Ala Phe Tyr Arg Trp Tyr Ala Lys
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 152

Ala Phe Phe Arg Trp Tyr Ala Lys
1               5

<210> SEQ ID NO 153
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 153

Ala Phe Gly Arg Trp Tyr Ala Lys
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 154

Ala Phe His Arg Trp Tyr Ala Lys
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 155

Ala Phe Ile Arg Trp Tyr Ala Lys
1               5

<210> SEQ ID NO 156
<211> LENGTH: 8
<212> TYPE: PRT
<213> ORGANISM: Artificial Sequence

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 156

Ala Phe Leu Arg Trp Tyr Ala Lys
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 157

Ala Phe Met Arg Trp Tyr Ala Lys
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 158

Ala Phe Asn Arg Trp Tyr Ala Lys
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 159

Ala Phe Pro Arg Trp Tyr Ala Lys
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 160

Ala Phe Gln Arg Trp Tyr Ala Lys
1               5
```

```
<210> SEQ ID NO 161
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 161

Ala Phe Arg Arg Trp Tyr Ala Lys
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 162

Ala Phe Ser Arg Trp Tyr Ala Lys
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 163

Ala Phe Thr Arg Trp Tyr Ala Lys
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 164

Ala Phe Val Arg Trp Tyr Ala Lys
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
```

```
<400> SEQUENCE: 165

Ala Phe Tyr Arg Trp Tyr Ala Lys
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 166

Ala Phe Tyr Phe Trp Tyr Ala Lys
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 167

Ala Phe Tyr Gly Trp Tyr Ala Lys
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 168

Ala Phe Tyr Leu Trp Tyr Ala Lys
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 169

Ala Phe Tyr Met Trp Tyr Ala Lys
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: ACETYLATION

<400> SEQUENCE: 170

Ala Phe Tyr Asn Trp Tyr Ala Lys
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 171

Ala Phe Tyr Pro Trp Tyr Ala Lys
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 172

Ala Phe Tyr Thr Trp Tyr Ala Lys
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 173

Ala Phe Tyr Val Trp Tyr Ala Lys
1               5

<210> SEQ ID NO 174
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 174

Ala Phe Tyr Trp Trp Tyr Ala Lys
1               5

<210> SEQ ID NO 175
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 175

Ala Phe Tyr Tyr Trp Tyr Ala Lys
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 176

Ala Lys Trp Phe Arg Tyr Ala Lys
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 177

Val Ser Arg Asn Trp Tyr Lys
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 178

Ala Ser Arg Asn Trp Tyr Ala Lys
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 179
```

```
Ala Ser Arg Phe Trp Tyr Ala Lys
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 180

Phe Ser Arg Asn Trp Tyr Ala Lys
1               5

<210> SEQ ID NO 181
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 181

Val Phe Arg Asn Trp Tyr Ala Lys
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 182

Val Trp Arg Asn Trp Tyr Ala Lys
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 183

Val Tyr Arg Asn Trp Tyr Ala Lys
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: ACETYLATION

<400> SEQUENCE: 184

Val Ser Arg Ala Trp Tyr Ala Lys
1               5

<210> SEQ ID NO 185
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 185

Val Ser Arg Phe Trp Tyr Ala Lys
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 186

Val Ser Arg Trp Trp Tyr Ala Lys
1               5

<210> SEQ ID NO 187
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 187

Val Ser Arg Tyr Trp Tyr Ala Lys
1               5

<210> SEQ ID NO 188
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 188

Val Ser Arg Asn Phe Tyr Ala Lys
1               5

<210> SEQ ID NO 189
<211> LENGTH: 8
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 189

Val Ser Arg Asn Tyr Tyr Ala Lys
1               5

<210> SEQ ID NO 190
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 190

Val Ser Arg Asn Trp Phe Ala Lys
1               5

<210> SEQ ID NO 191
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 191

Val Ser Arg Asn Trp Trp Ala Lys
1               5

<210> SEQ ID NO 192
<211> LENGTH: 4
<212> TYPE: PRT
<213> ORGANISM: Artificial Sequence
<220> FEATURE:
<223> OTHER INFORMATION: Synthetic peptide

<400> SEQUENCE: 192

Tyr Trp Lys Ala
1

<210> SEQ ID NO 193
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 193

Tyr Trp Lys Ala Lys
1               5

<210> SEQ ID NO 194
<211> LENGTH: 4
```

```
<212> TYPE: PRT
<213> ORGANISM: Artificial Sequence
<220> FEATURE:
<223> OTHER INFORMATION: Synthetic peptide

<400> SEQUENCE: 194

Tyr Lys Tyr Ala
1

<210> SEQ ID NO 195
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 195

Tyr Lys Tyr Ala Lys
1               5

<210> SEQ ID NO 196
<211> LENGTH: 4
<212> TYPE: PRT
<213> ORGANISM: Artificial Sequence
<220> FEATURE:
<223> OTHER INFORMATION: Synthetic peptide

<400> SEQUENCE: 196

Tyr Trp Arg Ala
1

<210> SEQ ID NO 197
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 197

Tyr Trp Arg Ala Lys
1               5

<210> SEQ ID NO 198
<211> LENGTH: 4
<212> TYPE: PRT
<213> ORGANISM: Artificial Sequence
<220> FEATURE:
<223> OTHER INFORMATION: Synthetic peptide

<400> SEQUENCE: 198

Ala Arg Trp Tyr
1

<210> SEQ ID NO 199
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: ACETYLATION

<400> SEQUENCE: 199

Ala Arg Trp Tyr Lys
1               5

<210> SEQ ID NO 200
<211> LENGTH: 4
<212> TYPE: PRT
<213> ORGANISM: Artificial Sequence
<220> FEATURE:
<223> OTHER INFORMATION: Synthetic peptide

<400> SEQUENCE: 200

Tyr Trp Arg Ala
1

<210> SEQ ID NO 201
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 201

Tyr Trp Arg Ala Lys
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic peptide

<400> SEQUENCE: 202

Ala Phe Met Arg Trp Tyr Ala
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic peptide

<400> SEQUENCE: 203

Ala Phe Asn Arg Trp Tyr Ala
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic peptide

<400> SEQUENCE: 204

Ala Phe Pro Arg Trp Tyr Ala
1               5

<210> SEQ ID NO 205
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 205

Ala Phe Gln Arg Trp Tyr Ala
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic peptide

<400> SEQUENCE: 206

Ala Phe Arg Arg Trp Tyr Ala
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic peptide

<400> SEQUENCE: 207

Ala Phe Ser Arg Trp Tyr Ala
1               5

<210> SEQ ID NO 208
<211> LENGTH: 229
<212> TYPE: PRT
<213> ORGANISM: Artificial Sequence
<220> FEATURE:
<223> OTHER INFORMATION: Synthetic peptide

<400> SEQUENCE: 208

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys Ala Asp Ala Gln Gln Asn Lys Phe
                165                 170                 175

Asn Lys Asp Gln Gln Ser Ala Phe Tyr Glu Ile Leu Asn Met Pro Asn
            180                 185                 190
```

```
Leu Asn Glu Glu Gln Arg Asn Gly Phe Ile Gln Ser Leu Lys Asp Asp
        195                 200                 205

Pro Ser Gln Ser Thr Asn Val Leu Gly Glu Ala Lys Lys Leu Asn Glu
    210                 215                 220

Ser Gln Ala Pro Lys
225
```

PRODUCTION OF RECOMBINANT PROTEINS BY AUTOPROTEOLYTIC CLEAVAGE OF A FUSION PROTEIN

This application is a Continuation of co-pending Application No. 11/919,257 filed on Aug. 8, 2008, and for which priority is claimed under 35 U.S.C. §120; which is the U.S. National Phase application under 35 U.S.C. §371 of International Application No. PCT/AT2006/000168 filed on Apr. 25, 2006; and which claims priority to Application No. 0508435.5 filed in Great Britain on Apr. 25, 2005, Application No. 0508434.8 filed in Great Britain on Apr. 26, 2005 and Application No. 0605379.7 filed in Great Britain on Mar. 16, 2006 under 35 U.S.C. §119; the entire contents of all are hereby incorporated by reference.

FIELD OF INVENTION

The present invention relates to a method for the production of a heterologous recombinant polypeptide of interest with a defined homogenous N-terminus. The present invention combines a chromatography system with a fusion polypeptide that comprises the polypeptide of interest and an additional part, a second polypeptide, which exhibits an autoproteolytic function and which is linked to the N-terminus of the polypeptide of interest. The chromatography system which forms part of the present invention allows for the activation of the autoproteolytic function of the N-terminal part of said fusion polypeptide while the fusion polypeptide is bound to the chromatography system. Binding, refolding and cleavage of the fusion polypeptide are conducted in the same chromatography system, from which the polypeptide of interest can then be isolated in its purified form.

BACKGROUND OF INVENTION

While most polypeptides of interest, e.g. pharmaceutically useful proteins, originate from eukaryotes, they are, due to high expression rates and high yields, usually produced in bacterial cells. However, the mechanism of polypeptide synthesis in bacteria differs from that in eukaryotes; polypeptides expressed in bacterial cells usually have either an additional foreign amino acid at the N-terminus or are inhomogenous in respect to their N-terminus, since cleavage of the additional amino acid can occur but remains incomplete most of the time.

Such inhomogeneity is however unacceptable in particular in the pharmaceutical field, because these polypeptides show properties that are different from the properties of the naturally occurring polypeptide, e.g. induction of antibody formation, half-life, pharmacokinetics etc. An N-terminus that deviates from the naturally occurring protein and/or is inhomogenous is an unacceptable feature. For the production of pharmaceutical polypeptides it is in most cases necessary to produce a nature-identical product (homogeneous with the correct N-terminus, which has no additional amino acids. The known methods attempt to reach this goal by incorporating additional steps in the process of polypeptide production, with expenditure of costs and materials, making further work up, the so-called downstream processing of the product, more complex.

Known methods for the production of a polypeptide in bacterial cells with a defined, homogenous N-terminus employ a fusion polypeptide comprising the polypeptide of interest and, N-terminally linked thereto, a polypeptide with autoproteolytic activity, preferably the autoprotease $N^{pro}$ of pestivirus. The autoproteolytic activity of the fusion partner leads to the cleavage of the polypeptide of interest with a homogenous N-terminus.

If a polypeptide is produced in the cytoplasm of bacterial cells, under certain conditions, the production rate of the polypeptide is faster than the folding kinetics. Therefore high density polypeptide aggregates are formed, which are deposited in the cytoplasm of the cell as inclusion bodies. The production of polypeptides in the form of inclusion bodies is of special interest for production on industrial scale, since the expressed polypeptide is present in the inclusion bodies in high amounts and a high degree of purity. Also, the inclusion bodies of the cell lack proteases, so that the polypeptide is protected when stored in inclusion bodies. In addition, inclusion bodies are easy to isolate. However, major drawbacks of production of polypeptides in the form of cytoplasmatic inclusion bodies are low solubility of the inclusion bodies and the necessity to refold the polypeptide.

Accordingly, processing of inclusion bodies is complex, especially since correct refolding is required in order to gain the biologically active form of the polypeptide of interest. Therefore, although the use of the autoproteolytic activity of a fusion polypeptide as described above consistently leads to the production of a polypeptide with a homogenous N-terminus, the process of purification of the desired product remains tedious, especially if it is expressed in form of cytoplasmatic inclusion bodies. The processing involves numerous steps including washing, refolding, cleavage, purification, and isolation.

Thus, the complex downstream processing poses a big challenge with regard to fast and cost effective production of polypeptides. This is exceedingly the case for production on industrial scale. Accordingly, there is an ongoing need for a simple and feasible process for production and purification of polypeptides.

SUMMARY OF THE INVENTION

Within the scope of the present invention it has now surprisingly been found that a process for obtaining a heterologous polypeptide of interest e.g. from inclusion bodies, can be greatly facilitated by the combination of a specific affinity chromatography method with a fusion polypeptide system, which exerts autoproteolytic activity. Thus the processing can be conducted in a concerted action in one chromatography system.

Initially the fusion polypeptide is provided. This fusion polypeptide comprises a polypeptide having autoproteolytic function, preferably the autoproteolytic function of an autoprotease, more preferably the autoproteolytic function of the autoprotease $N^{pro}$ of Pestivirus, as well as derivatives thereof. C-terminally of the polypeptide with autoproteolytic function, said fusion polypeptide comprises the heterologous polypeptide of interest.

The fusion polypeptide is produced in a host cell under conditions that inhibit the autoproteolytic activity of its N-terminal part. In particular the fusion polypeptide is produced in a denatured form in cytoplasmatic inclusion bodies. These inclusion bodies are isolated from the cells and solubilized under conditions that preserve the inactivity. Then the fusion polypeptide is selectively bound to a chromatography system, in particular a column under conditions that keep the N-terminal part of the fusion polypeptide in its inactive, denatured state.

Once the fusion polypeptide is bound, if necessary, unbound contaminating components are washed out.

When only the fusion polypeptide is left bound to the chromatography system, the conditions in the thus purified system are changed from inhibiting to activating the autoproteolytic function. This change of conditions allows the fusion polypeptide to regain its native configuration, whereby the autoproteolytic function of its N-terminal part is activated and the polypeptide of interest is cleaved off, resulting in the elution of an already purified, refolded polypeptide of interest with a homogenous N-terminus, while the N-terminal part remains bound to the chromatography system.

Once the fusion polypeptide is bound, the steps of 1) washing out of unbound contaminating components, 2) refolding and 3) cleaving of the polypeptide of interest as well as 4) purifying the polypeptide of interest take place in the same chromatography system. This greatly facilitates the work up. Unbound contaminating components are easily washed out within this system, while the fusion polypeptide stays selectively bound to the chromatography system.

DETAILED DESCRIPTION OF THE INVENTION

A new method for the production of a heterologous polypeptide of interest with a homogenous N-terminus is provided, which greatly reduces the complex processing usually necessary in order to acquire active polypeptide.

Accordingly, the present invention relates to a method for the production of a heterologous polypeptide of interest with a homogenous N-terminus, using a fusion polypeptide comprising the polypeptide of interest and N-terminally thereto a polypeptide exhibiting autoproteolytic function, said method comprising the steps of a) binding of the fusion polypeptide in a soluble, autoproteolytically inactive form by an affinity chromatography system, b) refolding of the fusion polypeptide, thereby activating the autoproteolytic function of the fusion polypeptide and causing cleavage of the heterologous polypeptide of interest, and c) subsequently eluting the heterologous polypeptide of interest, wherein said steps are conducted on one affinity chromatography system.

As used herein the following terms shall have the meanings described below:

The term "heterologous polypeptide of interest" refers to a polypeptide which is not naturally cleaved by a naturally occurring autoprotease from a naturally occurring (fusion) polypeptide. Examples of heterologous polypeptides of interest are industrial enzymes (process enzymes) or polypeptides with therapeutic activity, in particular for the therapy of humans.

The term "fusion polypeptide" refers to a polypeptide consisting of two or more polypeptides. In particular, a fusion polypeptide may comprise an affinity tag, an autoproteolytic part, preferably an autoprotease, and a polypeptide of interest. In the meaning of the present invention, the fusion polypeptide comprises the polypeptide of interest and, N-terminally linked thereto, a polypeptide with an autoproteolytic function.

The term "denatured form" in the meaning of the present invention designates the biologically inactive form of the expressed fusion polypeptide, as obtained as a product of the recombinant production process, usually as obtained after solubilising the inclusion bodies.

The term "refolding" refers to the mechanism during which the solubilized polypeptide regains its native conformation and biological activity, i.e. reconstituting a protein from its denatured, inactive state to its active form.

The term "autoproteolytic function" refers to the autoproteolytic activity of one of the fusion partners, which is inhibited while the fusion polypeptide is in its denatured state and which is activated upon refolding of the fusion polypeptide.

The fusion polypeptide is bound to the chromatography system in a state, when its autoproteolytic functioning part is inactive. Binding has to be such that it is maintained during the change of conditions, cleavage of the polypeptide of interest, and thereafter. Within the scope of the present invention the initiation of cleavage is accomplished while the fusion polypeptide is refolded, whereby it is transferred from the inactive to the active state. The present invention provides a chromatographic affinity system, which establishes binding of the fusion polypeptide at its N-terminus under denaturizing conditions, and maintains binding of the fusion partner that exerts the autoproteolytic function through all changes of conditions which follow. Since the refolding takes place while the polypeptide is bound to the chromatography system, an additional requirement is that the affinity system does not interfere with the refolding process. Also this problem is solved by the present invention.

As used herein the term "denaturizing" shall mean conditions under which the native three dimensional structure of a polypeptide is disrupted.

In the autoproteolytically active part of the fusion polypeptide, refolding leads to an activation and thus initiation of cleavage. Simultaneously the polypeptide of interest part regains its native conformation, consequently, the cleaved polypeptide of interest is in its native, active form. Since the autoproteolytically active part of the fusion polypeptide remains bound to the column after cleavage, and since unbound contaminating components are washed from the column prior to initiation of cleavage, already purified, refolded polypeptide of interest is eluted from the column. Thus further work up for separation of the two parts of the fusion polypeptide, separation from cleavage agent or refolding is dispensable.

The fusion polypeptide within the scope of the present invention is provided by production within a bacterial host cell, in an initially inactive form.

In a preferred embodiment of the present invention the fusion polypeptide is provided by recombinant expression in a bacterial host cell in the form of inclusion bodies, utilizing a host cell that is transformed with an expression vector comprising a nucleic acid molecule which codes for the fusion polypeptide.

As used herein the term "inclusion bodies" shall refer to aggregates containing heterologous polypeptides present in the cytoplasm of transformed host cells. These appear as bright spots under the microscope and can be recovered by separation of the cytoplasm.

As used herein the term "transformed host cell" shall refer to a cell containing a vector coding for a heterologous polypeptide.

In order to initiate cleavage on the column, the autoproteolytic activity of the fusion polypeptide has to be inhibited from the start, already during expression of the polypeptide within the host cell. Expression under conditions that cause the deposition of the expressed polypeptide in the cytoplasm of the host cell, usually in form of inclusion bodies, the prerequisite of inactivity is met.

A bacterial host cell to be employed in accordance with the present invention can be, for example, gram-negative bacteria such as *Escherichia* species, for example *E. coli*, or other gram-negative bacteria, for example *Pseudomonas* sp., such as *Pseudomonas aeruginosa*, or *Caulobacter* sp., such as *Caulobacter crescentus*, or gram-positive bacteria such as *Bacillus* sp., in particular *Bacillus subtilis*. *E. coli* is particularly preferred as host cell.

The expression vector used in the method of the present invention comprises a nucleic acid molecule, which codes for a fusion polypeptide, comprising a polypeptide which exhibits autoproteolytic function and C-terminally thereto the polypeptide of interest. The cleavage is exerted at the C-terminal end of the autoproteolytically active polypeptide, resulting in a homogenous N-terminus of the desired polypeptide.

In a preferred embodiment of the present invention the polypeptide exhibiting autoproteolytic function is an autoprotease.

As used herein the term "autoprotease" shall refer to a polypeptide that possesses autoproteolytic activity and is capable of cleaving itself from a larger polypeptide moiety, preferably a naturally occurring autoprotease. The concept of autoproteases as such is well available to the skilled man in the art; many naturally occurring autoprotease systems are known. Well studied autoprotease systems are e.g. viral proteases, developmental proteins (e.g. HetR, Hedgehog proteins (the carboxyterminal autoprotease thereof), RumA autoprotease domain, UmuD, etc).

Viruses within the Flaviviridae, including the pestiviruses all have the NS3 proteases in common. It has been shown in yellow fever, dengue type 2 and West Nile viruses that the protease domain is located in the N-terminal ~180 residues of NS3 and is responsible for cleavage at the NS2A/2B and NS2B/NS3 junctions in an apparent intramolecular fashion. Analysis of hepatitis C and GB virus NS3 sequences showed a close relationship with flavi- and pestivirus NS3 sequences.

An N-terminal autoprotease is also encountered in aphthoviruses [foot-and-mouth disease virus (FMDV)], which are positive-strand RNA viruses belonging to the family Picornaviridae. This proteinase, also referred to as leader protease (Lpro), belongs to the papain family of cysteine-proteases. In addition to cleaving itself off the polyprotein, it causes the proteolytic degradation of the 220-kDa subunit of the eukaryotic initiation factor 4G and thus contributes to the shutoff of cap-dependent host cell protein synthesis. Since picornaviral RNA is not capped, it continues to be translated as the cap-binding protein complex is inactivated. However, the aphthovirus leader proteinase gene is not required for viral replication in cell culture.

Two other autoproteases of the picornavirus family are 2A and 3C, which have significant identity with chymotrypsin-like serine-proteases. Both proteases are contained within the polyprotein precursor. One short example for autoproteolysis in plant viruses is the leader proteinase of the Beet yellows virus, which possesses a non-conserved N-terminal domain (functions in RNA amplification) and a conserved, papain-like C-terminal domain required for autoproteolysis.

Autoproteases can also be found in retroviruses, such as in the Gag-Pol polyprotein of human immunodeficiency virus (HIV-1). The polyprotein comprises a 99 amino acid rotease that releases itself after dimerization with a second protease from another polyprotein.

More preferably the term "autoprotease" refers to the autoprotease $N^{pro}$ of a pestivirus, including all derivatives thereof with autoproteolytic activity.

The present invention relates to a further embodiment, wherein the autoprotease is $N^{pro}$ of a pestivirus, or a derivative thereof with autoproteolytic function.

Pestiviruses are small enveloped viruses with a genome which acts directly as mRNA. Two virus-encoded proteases that have been identified in Pestiviruses are the autoprotease $N^{pro}$ and the serine protease NS3. The protease $N^{pro}$ is located at the N-terminus of the polyprotein. $N^{pro}$ constitutes the first protein in the polyprotein of Pestiviruses and undergoes autoproteolytic cleavage from the following nucleocapsid protein. This cleavage takes place after the last amino acid in the sequence of $N^{pro}$, Cys168.

Pestiviruses form a group of pathogens which include amongst others, the classical swine fewer virus, (CSFV), the border disease virus (BDV) and the bovine viral diarrhoea virus (BVDV). Accordingly in a more preferred embodiment of the present invention, the pestivirus is selected from the group of CSFV, BDV and BVDV, with CSFV being particularly preferred.

In an even more preferred embodiment of the present invention the autoprotease $N^{pro}$ of CSFV has the following amino acid sequence:

```
SEQ ID NO 1:
(1)-MELNHFELLYKTSKQKPVGVEEPVYDTAGRPLFGNPSEVHPQSTLKLPHDRGRGDIRTTLR

DLPRKGDCRSGNHLGPVSGIYIKPGPVYYQDYTGPVYHRAPLEFFDEAQFCEVTKRIGRVTGS

DGKLYHIYVCVDGCILLKLAKRGTPRTLKWIRNFTNCPLWVTSC-(168),
``` or the amino acid sequence of a derivative thereof with autoproteolytic function.

See also EMBL database accession number X87939, amino acids 1 to 168, reading from N-terminal to the C-terminal direction.

Derivatives with autoproteolytic function according to the present invention are derived from the autoprotease $N^{pro}$ of a pestivirus by mutagenesis, in particular amino acid substitution, deletion, addition and/or amino acid insertion, as long as the required autoproteolytic activity, in particular for generating a desired heterologous polypeptide of interest with homogeneous N-terminus, is retained. Methods for generating such derivatives by mutagenesis are familiar to the skilled person. It is possible by such mutations to adapt the properties of the autoprotease $N^{pro}$ in relation to different heterologous polypeptides to be cleaved from the fusion polypeptide. In particular a polypeptide within the scope of the present invention can be designed to have improved properties compared to the originally occurring autoprotease, while still exhibiting the autoproteolytic activity of $N^{pro}$ of a pestivirus. Particularly preferred in this respect are derivatives, which show improved properties in respect of solubility as well as superior binding to the chromatographic affinity system, which properties are especially useful within the context of the present invention.

The autoproteolytic properties of derivatives obtained by mutagenesis can be tested as described e.g. in WO 01/11056.

Derivatives of the naturally occurring $N^{pro}$ of a pestivirus as depicted in sequence ID No 1 above are especially preferred, wherein cysteine residues are replaced. More preferred in this respect are derivatives of the naturally occurring $N^{pro}$, wherein the three cysteine residues C112, C134 and C138 are replaced by other amino acid residues, e.g. glutamic acid. A particularly preferred derivative comprises the following amino acid sequence:

SEQ ID NO 2:
(1)-MELNHFELLYKTSKQKPVGVEEPVYDTAGRPLFGNPSEVHPQSTLKLPHDRGRGDIRTTLR

DLPRKGDCRSGNHLGPVSGIYIKPGPVYYQDYTGPVYHRAPLEFFDEAQFEEVTKRIGRVTGS

DGKLYHIYVEVDGEILLKLAKRGTPRTLKWIRNFTNCPLWVTSC-(168)

Another preferred derivative of the naturally occurring N$^{pro}$ of a pestivirus, is the one wherein in addition to the cysteine mutations described above, the arginines in positions 53 and 57 are exchanged to glutamic acid residues, glycine 54 is exchanged to aspartic acid and leucin 143 to glutamine. This derivative comprises the following amino acid sequence:

SEQ ID NO 3:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDEAQFEEVTKRIGRVTGS

DGKLYHIYVEVDGEILLKQAKRGTPRTLKWIRNFTNCPLWVTSC-(168)

Thus in another aspect the present invention also relates to a process as described above, wherein the fusion polypeptide comprises a derivative of an autoprotease N$^{pro}$ of CSFV, wherein in addition to the replacement of at least one cysteine residue as described above, at least one hydrophobic amino acid residue is replaced by a hydrophilic residue.

Preferred within the present invention is a derivative of an autoprotease N$^{pro}$ of CSFV, wherein in addition to the replacement of at least one cysteine residue as described above furthermore at least one of the following amino acids are replaced: V24, A27, L32, G54, L75, A109, V114, V121, L143, I155 and F158. A preferred example is a derivative wherein the following amino acids are exchanged by threonine (T): alanine (A) 109, valine (V) 114, isoleucine (I) 155 and phenylalanine (F)158.

Thus in another aspect the present invention relates preferably to a process as described above, wherein the fusion polypeptide comprises a derivative of an autoprotease N$^{pro}$ of CSFV, wherein in addition to the replacement of at least one cysteine residue as described above, the following amino acids are replaced by threonine (T): alanine (A) 109, valine (V) 114, isoleucine (I)155 and phenylalanine (F)158. Another, within the present invention more preferred derivative of an autoprotease N$^{pro}$ of CSFV, comprises the following amino acid sequence:

SEQ ID NO 4:
(1)-MELNHFELLYKTSKQKPVGVEEPVYDTAGRPLFGNPSEVHPQSTLKLPHDRGRGDIRTTLR

DLPRKGDCRSGNHLGPVSGIYIKPGPVYYQDYTGPVYHRAPLEFFDETQFEETTKRIGRVTGS

DGKLYHIYVEVDGEILLKLAKRGTPRTLKWTRNTTNCPLWVTSC-(168)

Thus in another aspect the present invention more preferably relates to a process as described above, wherein the fusion polypeptide comprises a derivative of an autoprotease N$^{pro}$ of CSFV having a sequence according to SEQ ID NO 4.

Even more preferred within the present invention is a derivative of an autoprotease N$^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T), arginine (R) 53 with glutamic acid (E), glycine (G) 54 with aspartic acid (D), arginine (R) 57 with glutamic acid (E), and leucine (L) 143 with glutamine (Q).

Thus in another aspect the present invention relates even more preferably to a process as described above, wherein the fusion polypeptide comprises a derivative of an autoprotease N$^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T); arginine (R) 53 with glutamic acid (E), glycine (G) 54 with aspartic acid (D), arginine (R) 57 with glutamic acid (E), and leucine (L) 143 with glutamine (Q).

Most preferably the derivative of an autoprotease N$^{pro}$ of CSFV according to the present invention comprises the following amino acid sequence:

SEQ ID NO 5:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDETQFEETTKRIGRVTGS

DGKLYHIYVEVDGEILLKQAKRGTPRTLKWTRNTTNCPLWVTSC-(168).

Thus in another, most preferred aspect the present invention also relates to a process as described above, wherein the fusion polypeptide comprises a derivative of an autoprotease N$^{pro}$ of CSFV having a sequence according to SEQ ID NO 5.

In another equally preferred aspect the present invention relates to a process for the production of heterologous proteins as described above, wherein the fusion polypeptide comprises a derivative of an autoprotease N$^{pro}$ of CSFV having a sequence according to SEQ. ID NO. 5, wherein in addition asparagine (N) 35 is replaced with threonine (T), and threonine (T) 158 is replaced with serine (S).

The derivative of an autoprotease N$^{pro}$ of CSFV which is utilized in the process according to the above aspect of the present invention forms also part of the present invention and comprises the following amino acid sequence:

SEQ ID NO 32:
(1)-MELNHFELLYKTSKQKPVGVEEPVYDTAGRPLFGTPSEVHPQSTLKLPHDRGEDDIETTLR

DLPRKGDCRSGNHLGPVSGIYIKPGPVYYQDYTGPVYHRAPLEFFDETQFEETTKRIGRVTGS

DGKLYHIYVEVDGEILLKQAKRGTPRTLKWTRNSTNCPLWVTSC-(168).

In another preferred aspect the present invention relates to a process for the production of heterologous proteins as described above, wherein the fusion polypeptide comprises a derivative of an autoprotease N$^{pro}$ of CSFV having a sequence according to SEQ. ID NO. 32, wherein in addition alanine (a) 28 is replaced with glutamic acid (E), serine (S) 71 is replaced with phenylalanine (F) and arginine (R) 150 is replaced with histidine (H).

The derivative of an autoprotease N$^{pro}$ of CSFV which is utilized in the process according the above aspect of the present invention forms also part of the present invention and comprises the following amino acid sequence:

SEQ ID NO 33:
(1)-MELNHFELLYKTSKQKPVGVEEPVYDTEGRPLFGTPSEVHPQSTLKLPHDRGEDDIETTLR

DLPRKGDCRFGNHLGPVSGIYIKPGPVYYQDYTGPVYHRAPLEFFDETQFEETTKRIGRVTGSD

GKLYHIYVEVDGEILLKQAKRGTPHTLKWTRNSTNCPLWVTSC-(168).

Preferably in the process according to the present invention the derivative of an autoprotease N$^{pro}$ of CSFV with the sequence according to SEQ ID NO 32 is used in fusion with a protein that contains at least the three first amino acids of proinsulin, more preferably with proinsulin, further more preferably with human proinsulin, most preferably with recombinant human proinsulin, for the production of proinsulin.

It is preferred according to the present invention if the derivative of an autoprotease N$^{pro}$ of CSFV has in addition to the replacement of at least one cysteine residue as described above at least one of the following amino acids have been exchanged: arginine (R) 53, glycine (G) 54, arginine (R) 57, threonine (T) 109, 114, 155, 158 and leucine (L) 143. Preferred derivatives of the autoprotease N$^{pro}$ of CSFV according to the present invention have in addition to the replacement of at least one cysteine residue as described above, the following amino acids are exchanged: arginine (R) 53 with glutamic acid (E), glycine (G) 54 with aspartic acid (D), arginine (R) 57 with glutamic acid (E), threonine (T) 109, 114, 155, 158 with serine (S) and leucine (L) 143 with glutamine (Q) or asparagine (N) or aspartic acid (D) or serine (S) or histidine:

Such preferred derivatives of an autoprotease N$^{pro}$ of CSFV which are utilized in the process according the above aspect of the present invention forms also part of the present invention and comprise the following amino acid sequences:

SEQ ID 92:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDESQFEESTKRIGRVTGS

DGKLYHIYVEVDGEILLKSAKRGTPRTLKWSRNSTNCPLWVTSC-(168).

SEQ ID 95:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDESQFEESTKRIGRVTGS

DGKLYHIYVEVDGEILLKNAKRGTPRTLKWSRNSTNCPLWVTSC-(168).

SEQ ID 96:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDESQFEESTKRIGRVTGS

DGKLYHIYVEVDGEILLKDAKRGTPRTLKWSRNSTNCPLWVTSC-(168).

SEQ ID 97:
(1)-MELNHFELLYKTSKQKPVGVEEPVYDTAGRPLFGNPSEVHPQSTLKLPHDRGEDDIETTLR

DLPRKGDCRSGNHLGPVSGIYIKPGPVYYQDYTGPVYHRAPLEFFDESQFEESTKRIGRVTGS

DGKLYHIYVEVDGEILLKHAKRGTPRTLKWSRNSTNCPLWVTSC-(168).

SEQ ID 98:
(1)-MELNHFELLYKTSKQKPVGVEEPVYDTAGRPLFGNPSEVHPQSTLKLPHDRGEDDIETTLR

-continued

DLPRKGDCRSGNHLGPVSGIYIKPGPVYYQDYTGPVYHRAPLEFFDESQFEESTKRIGCVTGS

DGKLYHIYVEVDGEILLKQAKRGTPRTLKWSRNSTNCPLWVTSC-(168).

The expression vector encodes the polypeptide of interest as the part of the fusion polypeptide which is to be cleaved off autoproteolytically. In accordance with the present invention, a variety of polypeptides of interest can be produced by use of such an expression vector. For example, the polypeptide of interest is one, that exerts pharmacological activity and can for example be selected from the group consisting of an interferon, an interleukin, a growth hormone, a growth factor, a cytokine, an enzyme, an enzyme inhibitor, an antibody and an antibody fragment, and the like, for example interferon alpha 2A, interferon alpha 2B, interleukin-3, interleukin-6, human growth hormone, (pro)insulin, insulin like growth factor, granulocyte-colony stimulating factor, granulocyte macrophage-colony stimulating factor, macrophage-colony stimulating factor, interferon beta 1, bovine somatropin, porcine somatropin, interleukin 11, interleukin-2, a Fab-fragment, and small peptides such as calcitonin, parathyroid hormone (PTH), or a glucagon, CD 40 ligand soluble form, plasminogen activator, sex steroid binding protein, epidermal growth factor, tissue factor extra cellular domain.

In addition the polypeptide of interest can be any other kind of polypeptide in particular a polypeptide which is especially suited for analytical methods, e.g. Green Fluorescent Protein.

In the expression vector to be employed in the process according to the present invention, the fusion polypeptide is operably linked to at least one expression control sequence. Expression control sequences are, in particular, promoters (such as the lac, tac, T3, T7, trp, gac, vhb, lambda pL or phoA promoter), ribosome binding sites (for example natural ribosome binding sites which belong to the abovementioned promoters, cro or synthetic ribosome binding sites), or transcription terminators (for example rrnB T1T2 or bla).

The vector may also contain sequences encoding fusion domains, as described below, that are present at the N-terminal end of the fusion polypeptide and that are required for its binding to the affinity chromatography system, e.g. polyamino acids like polylysine or, for immunoaffinity chromatography, so-called "epitope tags", which are usually short peptide sequences for which a specific antibody is available. Well known epitope tags for which specific monoclonal antibodies are readily available include FLAG, influenza virus haemagglutinin (HA), and c-myc tags.

In a preferred embodiment of the present invention, the expression vector is a plasmid.

The transformed bacterial host cell, i.e. the expression strain, is cultivated in accordance with microbiological practice known per se.

The host strain is generally brought up starting from a single colony on a nutrient medium, but it is also possible to employ cryo-preserved cell suspensions (cell banks). The strain is generally cultivated in a multistage process in order to obtain sufficient biomass for further use. On a small scale, this can take place in shaken flasks, it being possible in most cases to employ a complex medium (for example LB broth). However, it is also possible to use defined media (for example citrate medium). Since in the preferred embodiment of the present invention it is intended that the expressed fusion polypeptide is in the form of insoluble inclusion bodies, the culture will in these cases be carried out at relatively high temperature (for example 30° C. or 37° C.). Inducible systems are particularly suitable for producing inclusion bodies (for example with the trp, lac, tac or phoA promoter).

On a larger scale, the multistage system consists of a plurality of bioreactors (fermenters), it being preferred to employ defined nutrient media. In addition, it is possible greatly to increase biomass and product formation by metering in particular nutrients (fed batch). Otherwise, the process is analogous to the shaken flask.

In the process according to the present invention, the inclusion bodies are isolated from the host cell in a manner known per se.

For example, after the fermentation has taken place, the host cells are harvested by centrifugation, micro filtration, flocculation or a combination thereof, preferably by centrifugation. The wet cell mass is disintegrated by mechanical, chemical or physical means such as high pressure homogenizer, beads mills, french press, hughes press, osmotic shock, detergents, enzymatic lysis or a combination thereof. Preferably, disruption of the cells takes place by high pressure homogenization. In the preferred embodiment where the recombinant fusion polypeptide is deposited as inclusion bodies, the inclusion bodies can be obtained for example by means of high-pressure dispersion or, preferably, by a simple centrifugation at low rotor speed. The inclusion bodies are separated by centrifugation or microfiltration or a combination thereof. The purity in relation to the desired polypeptide of interest can then be improved by multiple resuspension of the inclusion bodies in various buffers, for example in the presence of NaCl (for example 0.5-1.0 M) and/or detergent (for example Triton X-100). Preferably the purity of the inclusion body preparation is improved by several washing steps with various buffers (e.g. 0.5% Deoxycholate followed by two times 1 M NaCl solution—and finally distilled water). This usually results in removal of most of the foreign polypeptides from the inclusion bodies.

In preparation for the affinity chromatography, the isolated inclusion bodies need to be solubilized.

The present invention relates to a process as described above, where prior to application to the chromatography system, the provided fusion polypeptide is solubilized under chaotropic conditions that inhibit its autoproteolytic activity.

As used herein the term "chaotropic" shall refer to conditions where no or little intra-molecular interactions can be observed. These conditions can be achieved for example by addition of detergents, alcohol, urea or guanidine HCl. Conditions may differ for different polypeptides. However it is within the competency of the person skilled in the art to adjust conditions accordingly for any respective polypeptide.

The inclusion bodies are solubilized using a chaotropic agent. Upon solubilization inclusion bodies are dissolved and a monomolecular suspension with substantially reduced intra- and inter-molecular interactions is obtained. Preferred solvents are urea, guanidine HCl and strong ionic detergents as N-lauroylsarcosine. In another embodiment of the present invention inclusion bodies are also solubilized using an aqueous alcohol solution at alkaline pH or simply an aqueous solution at alkaline pH.

As used herein the term "solubilization" shall refer to the process necessary to dissolve the inclusion bodies. Solubilization results in a monomolecular dispersion of the polypeptides with minimum intra- and inter-molecular interactions.

A preferred way of solubilization of inclusion bodies within the scope of the present invention, is conducted by suspension in 50 mM Tris/HCl, 8 M urea, pH 7.3, adding a reducing agent, e.g. 50 mM DTT, in the case that oxidized cysteine residues are present.

Where necessary it is possible to remove potentially insoluble material, for example by centrifugation.

In the case that the inactive fusion polypeptide is produced soluble within the cell, the clarified cell homogenate is subjected to the further work up described in the following for the solubilized inclusion bodies.

The solubilized polypeptide is further diluted and applied to the chromatography system by loading it onto the affinity chromatography column. Within the scope of the present invention the chromatography system is adjusted such that the part of the fusion polypeptide that exhibits the autoproteolytic function is selectively recognized and bound under denaturizing, chaotropic conditions. Under these conditions the fusion polypeptide is denaturized, and inactive. In the course of the processing of the polypeptide on the column, conditions are changed to renaturazing, cosmotropic, with the result that the fusion polypeptide folds back into its native configuration and the autoproteolytic function is activated. The binding of the part exerting the autoproteolytic function is maintained during the change of conditions.

As used herein the term "cosmotropic" shall refer to conditions that promote molecular interactions and therefore formation of biological structures. Conditions may differ for different molecules. Citrate, and sulfate ions as anions and quarternary amines or ammonium ions as cations exhibit the highest cosmotropic effect. Also other reagents, such as detergents or redox systems, may be introduced to promote refolding. It is within the competency of a person skilled in the art to adjust conditions accordingly for every respective polypeptide.

In principle any chromatography system capable of selectively binding fusion polypeptides under chaotropic conditions and maintaining binding under cosmotropic conditions can be used within the framework of the present invention. The matrix of the chromatography system may, in a preferred embodiment, be in the form of a column, however, it may also be in other forms, like beads or organic materials like polyethylene glycol modified with an affinity peptide.

Chromatography systems suitable for use within the present invention may be based on a cellulose binding domain, they may be cation exchange chromatography systems using polycationic tags like e.g. polyarginine or polylysine as well as anion exchange chromatography with polyanionic tags like e.g. polyasparagine.

Accordingly within the present invention the affinity chromatography system is preferably selected from the group consisting of immobilized metal ion chromatography (IMAC), cation exchange chromatography, anion exchange chromatography, cellulose binding domain chromatography and peptide affinity chromatography.

More preferably the affinity chromatography system used is cation exchange chromatography, wherein the fusion polypeptide comprises a polycationic tag. Even more preferred is the use of either a polyarginine or polylysine affinity tag.

For cation exchange chromatography the expressed fusion polypeptide comprises an N-terminal polycationic tag, for example a polyarginine or polylysine tag. The solution containing the expressed fusion polypeptide that was extracted from the host cells is (filtered) and loaded onto a column packed with any medium suitable for cation exchange chromatography such as e.g. SP Sepharose FF, CM Sepharose FF, Fractogel EMD $SO^{3-}$. Preferably buffers with low conductivity are applied. After loading unbound material may be washed out and refolding may be started by introduction of a buffer with low urea concentration. At a urea concentration lower than 0.5M the target protein is cleaved off and can be eluted from the column.

Another preferred embodiment of the present invention is one, wherein the affinity chromatography system is anion exchange chromatography and wherein the fusion polypeptide comprises a polyanionic tag, More preferably, polyasparagine is used as affinity tag.

A further preferred embodiment to achieve the desired binding properties is immobilized metal ion affinity chromatography (IMAC).

Accordingly, in a preferred embodiment of the present invention the affinity chromatography system is immobilized metal ion affinity chromatography (IMAC), and the fusion polypeptide comprises a metal chelate affinity tag.

In this case the fusion polypeptide is detected and bound by means of a metal chelate affinity tag comprised in it.

In a more preferred embodiment of the present invention, the metal chelate affinity tag is a polyhistidine affinity tag.

IMAC is based on the specific coordinate covalent binding between histidine or other suitable unique amino acids (either naturally present on the surface of the protein or grafted with recombinant DNA techniques) and various immobilized metal ions, such as copper, nickel, zinc, or iron. Chromatographic materials known in the art for the use in IMAC may also be useful within the present invention. In a preferred embodiment of the present invention, $Ni^{2+}$-Chelating Sepharose Fast flow (GE Healthcare, Uppsala, SE) is used as matrix.

Alternatively, the affinity chromatography may be immunoaffinity chromatography, employing epitope tags as described above which are present at the N-terminus of the fusion polypeptide and are bound to the chromatographic matrix via an antibody recognizing said tag.

Another, within the scope of the present invention a preferred affinity chromatographic method, which has the required binding properties, is affinity chromatography using oligopeptide ligands.

As used herein the term "oligopeptides" shall refer to proteinaceous compounds, containing at least three amino acids. Usually such oligopeptides have a length of up to 35 amino acids.

Accordingly, in a preferred embodiment of the present invention the affinity chromatography system utilizes an oligopeptide ligand of five to twelve amino acids length, more preferred of six to eight amino acids length, comprising a tryptophan residue, which ligand selectively binds to the part of the fusion polypeptide exerting autoproteolytic function under chaotropic conditions and maintains binding during change towards as well as under cosmotropic conditions.

This form of affinity chromatography makes use of the specific binding of certain polypeptides to other polypeptides, as for example known from antibodies. Oligopeptides are capable of serving as affinity ligands as well. These molecules offer high chemical stability, efficiency, selectivity, low price and they are usually not toxic. These features are considered as an advantage especially when applied in a biopharmaceutical process. Peptide ligands directed against a target molecule can be identified from combinatorial peptide libraries or biological libraries in a way, known to the person skilled in the art. In the context of the present invention, screening for peptide ligands was performed under chaotropic conditions.

Methods for peptide synthesis known in the art, are suitable for preparation of the oligopeptide ligands which are subject to the present invention. Preferably though, the peptide ligands are generated by SPOT synthesis, PIN synthesis, teabag synthesis, mix and split method, described in Rulwu Liu, et al. Experimental Hematology 31 (2003) 11-30 or the PELICAN method, described in Joseph A. Buettner et al., Int. J. Peptide Protein Res. 47 (1996), 70-83. Several linker chemistries can be applied for anchoring of the first amino acid. In one preferred embodiment of the present invention, the ligands are generated separately and afterwards immobilized on the chromatographic matrix. In another preferred embodiment of the present invention, the peptide ligands are synthesized directly on the chromatographic matrix.

The oligopeptide ligand exerts a high degree of specificity. The oligopeptides that are synthesized within the scope of the present invention are characterized by their ability to selectively bind $N^{pro}$, $N^{pro}$ derivatives and fusion polypeptides thereof under denaturing conditions. Within the scope of the present invention such an oligopeptide ligand is directed against the part of the fusion polypeptide according to the invention that exerts autoproteolytic function.

In a further preferred embodiment of the present invention the oligopeptide ligand has an amino acid sequence selected from the group consisting of

```
SEQ ID NO 6:       VSIFEW,
SEQ ID NO 7:       AVSIEWY,
SEQ ID NO 8:       AVSFIWY,
SEQ ID NO 9:       VSFIWYK,
SEQ ID NO 10:      ASRFWYA,
SEQ ID NO 11:      AFYTWYA,
SEQ ID NO 12:      AFYRWYK,
SEQ ID NO 13:      AFYRWY,
SEQ ID NO 14:      AFYRWYA,
SEQ ID NO 15:      AVSIFEWY,
SEQ ID NO 16:      AVSRNWY,
SEQ ID NO 17:      ASRFWY,
SEQ ID NO 18:      AFYRWYAA,
SEQ ID NO 19:      AFYRWY,
SEQ ID NO 20:      ASRFWYAA,
SEQ ID NO 21:      AFYRWYAA,
SEQ ID NO 22:      AFYSWYAA.
```

Within the scope of the present invention oligopeptide ligands may be used with a free N-terminus or with a blocked N-terminus, blocking being achieved e.g. by acetylation.

Most preferred is an embodiment of the present invention, wherein the derivative of the naturally occurring $N^{pro}$ of CSFV according to SEQ ID NO 5 is used in combination with an oligopeptide ligand selected from the group consisting of SEQ ID NO 10, SEQ ID NO 11, SEQ ID NO 12, SEQ ID NO 13 and SEQ ID NO 14.

Therefore, the present invention also provides an affinity matrix comprising a solid phase and an affinity ligand comprising peptide bonds coupled to this solid phase, wherein the affinity ligand comprising peptide bond is selected from the following group of ligands:

a) peptides comprising the formula $X_1X_2X_3X_4$, wherein $X_1$ to $X_4$ are amino acid residues and at least two of $X_1$ to $X_4$ is W, Y or F;
b) peptides comprising the formula $X_5X_5X_7X_8$, wherein $X_5$ to $X_8$ are amino acid residues, at least one of $X_5$ to $X_8$ is W, and at least one of $X_5$ to $X_8$ is E or D; and
c) poly-amino acids consisting of an amino acid monomer of the group consisting of R, K, E and D and an amino acid monomer of the group consisting of Y, F and W, preferably poly-KY, poly-KF, poly-KW, poly-RY, poly-RF, poly-RW, poly-EY, poly-DY, poly-EF, poly-EW, poly-DF and poly-DW, with the proviso that the peptides according to a) and b) have a maximum length of 35 amino acid residues and that the poly-amino acids according to c) have a minimum length of 20 amino acid residues.

These affinity ligands have a high affinity to the autoprotease molecules described herein, especially to bind $N^{pro}$, its derivatives and fusion proteins thereof. Specifically, these ligands or affinity matrices bind $N^{pro}$, its derivatives and fusion proteins thereof under chaotropic conditions and also under kosmotropic conditions, at least the $N^{pro}$-part of e.g. a fusion protein.

Preferably, the peptides according to a) and b) (herein also referred to as "oliogopeptides") have a length of 5 to 12, especially of 6 to 8, amino acid residues. Preferably, at least one positively charged amino acid is present in these oligopeptides. The poly-amino acids according to c) have a preferred length of at least 35 amino acid residues, more preferred at least 50 amino acid residues, especially at least 100 amino acid residues. Specifically preferred poly-amino acids are e.g. commercially available poly-amino acids for culture media, such as poly-KW, 4:1 (MW 20.000-50.000 Da; SIGMA product No. P9285), poly-KY, 4:1 (MW 20.000-50.000 Da; SIGMA product No. P4695) or poly-KF, 1:1 (MW 20.000-50.000 Da; SIGMA product No. P3150).

The affinity ligand according to the present invention may be chemically modified, especially acetylated, esterified, amidated, oxidised, reduced or provided with a linker molecule.

The affinity ligand is preferably linked to the solid matrix by covalent bonds.

As solid phase material, all materials already applied in the present field are appropriate. Preferably, the solid phase is selected from the group consisting of chromatography material, especially supports based on cellulose, agarose, acrylamide, poly(styrene-divinylbenzene) or ethylene glycol-methacrylate copolymers, microtiter plates, nitrocellulose membranes, microchips, glass plates or metal coated supports.

According to the present invention various types of solid phase supports may be used, such as the supports based on cellulose, agarose (Sepharose or Macro-Prep gels), dextran (Sephadex gels), acrylamide (Sephacryl, Trisacryl gels), silica (TSK, SW gels), poly(styrene-divinylbenzene) (Source or Poros gels), ethylene glycol-methacrylate copolymers (Toyopearl HW, TSK, PW, fractogel EMD gels) or mixtures, in particular of agarose and dextran (Superdex gel). The supports approved for human or veterinary use by the competent American authorities (FDA for food and drug administration) or the European Union agencies will be more particularly selected. In addition, the support selected must be bonded, preferably by covalent bonding, to the affinity ligand according to the present invention (the support is said to be functionalized). The solid phase matrix may comprise, as the matrix backbone, any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly(meth)acryl-amides, polyvinylalcohols, silicas, and controlled pore glasses.

Especially interesting solid phase materials as matrix backbones are e.g. agar or agarose beads such as Sepharose and Superose beads from Pharmacia Biotech, Sweden and Biogel A from Biorad, USA; dextran based beads such as Sephadex, Pharmacia Biotech; cellulose based beads and membranes such as Perlaza cellulose from Secheza, Czechoslovakia; composite beads such as Sephacryl and Superdex, Pharmacia Biotech; beads of synthetic organic polymers such as Fractogel from Toso-Haas, USA; POROS media from Perceptive Biosystems, USA, Bio-Rex, Bio-Gel P and Macro Prep from Biorad, HEMA and Separon from TESSEK and Hyper D and Trisacryl media from BioSepra, USA, Enzacryl and Azlactone, 3M, USA; beads of siliceous materials such as controlled pore glass, PROSEP, from Bioprocesing, England and Spherocil, BioSepra; and coated silica composites in the form of beads or membranes such as ACTI-DISK, ACTI-MOD and CycloSep from Arbor Technologies, USA.

Typically, the solid phase matrix backbone, as well as the resulting functionalised solid phase matrix, may, e.g., be in the form of irregular particles or spherical beads, membranes or sheets, moulded surfaces, or sticks. The solid phase material may further be fully or partly permeable or completely impermeable to proteins. In a particularly interesting embodiment of the present invention, the matrix is in the form of irregular or spherical beads with sizes in the range of 1-10000 μm, preferably 10-1000 μm; such as 10-60 μm for high performance applications and such as 50-500 μm, preferably 50-300 μm, for preparative purposes.

A particular interesting form of matrix is a density controlled matrix in the form of a conglomerate comprising density controlling particles. These conglomerates, which are especially applicable in large scale operations for fluidised or expanded bed chromatography as well as different batch-wise chromatography techniques in non-packed columns, e.g. simple batch adsorption in stirred tanks.

The affinity ligands according to the present invention may be attached to the solid phase material by any type of covalent bond known per se to be applicable for this purpose, either by a direct chemical reaction between the affinity ligand according to the present invention and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

Especially interesting activating reagents are believed to be epoxy-compounds such as epichlorohydrin, allyl-glycidylether and butanedioldiglycidylether.

For peptide affinity chromatography within the scope of the present invention, any matrix useful for the immobilization of peptide ligands can be used. Preferably Fractogel epoxy (M), from Merck, Darmstadt, Germany) or equally preferred "monolithic chromatography medium" CIM-epoxy is used. The ligands can be immobilized either directly onto the chemically activated backbone of the chromatography matrix, or via a spacer or linker. In the latter case a spacer is coupled to the chromatographic matrix, said spacer is then chemically activated, in order to allow binding of the ligand. Preferably Fractogel epoxy matrices are used in combination with spacers.

In a particularly preferred embodiment of the present invention the spacer is generated by reaction of the chromatographic matrix with diaminodipropylamine (DADPA) and subsequent reaction with succinic anhydride (SA). The resulting terminal carboxy group on the spacer is chemically activated and preferably linked to a terminal amino-group. The ligand is immobilized on the matrix or on the spacer via a reactive group that it comprises. In the case of peptide ligands such reactive groups may be either the amino, carboxy or the sulfhydryl group. Within the present invention anchorage of the peptide on the matrix or the spacer via an amino bond is particularly preferred.

Preferably, the affinity matrix according to the present invention, especially provided as affinity chromatography material, exhibits oligopeptide ligands as defined under a) and b) above.

As used herein the term "oligopeptides" shall refer to proteinaceous compounds, containing at least three amino acids. Usually such oligopeptides have a length of up to 35 amino acids, preferably a length of 4 to 20 amino acid residues.

Accordingly, in a preferred embodiment of the present invention the affinity chromatography system utilizes an oligopeptide ligand of five to twelve amino acids length, more preferred of six to eight amino acids length, especially comprising a tryptophan residue, which ligand selectively binds to the part of the fusion polypeptide exerting autoproteolytic function under chaotropic conditions and maintains binding during change towards as well as under cosmotropic conditions.

This form of affinity chromatography makes use of the specific binding of certain polypeptides to other polypeptides, as for example known from antibodies. Oligopeptides are capable of serving as affinity ligands as well. These molecules offer high chemical stability, efficiency, selectivity, low price and they are usually not toxic. These features are considered as an advantage especially when applied in a biopharmaceutical process. Peptide ligands directed against a target molecule can be identified from combinatorial peptide libraries or biological libraries in a way, known to the person skilled in the art. In the context of the present invention, screening for peptide ligands was performed under chaotropic conditions.

These affinity ligands according to the present invention have turned out to be specifically characterized by their ability to bind N$^{pro}$ and N$^{pro}$-fusion proteins (and proteins being or comprising mutants thereof) under denaturing conditions, e.g. 4 M urea.

Methods for peptide synthesis known in the art, are suitable for preparation of the oligopeptide ligands which are subject to the present invention. Preferably though, the peptide ligands are generated by SPOT synthesis, PIN synthesis, teabag synthesis, mix and split method, described in Rulwu Liu, et al. Experimental Hematology 31 (2003) 11-30 or the PELICAN method, described in Joseph A. Buettner et al., Int. J. Peptide Protein Res. 47 (1996), 70-83. Several linker chemistries can be applied for anchoring of the first amino acid. In one preferred embodiment of the present invention, the ligands are generated separately and afterwards immobilized on the chromatographic matrix. In another preferred embodiment of the present invention, the peptide ligands are synthesized directly on the chromatographic matrix.

The oligopeptide ligand exerts a high degree of specificity. The oligopeptides that are synthesized within the scope of the present invention are characterized by their ability to selectively bind N$^{pro}$, N$^{pro}$ derivatives and fusion polypeptides thereof under denaturing conditions. Within the scope of the present invention such an oligopeptide ligand is directed against the part of the fusion polypeptide according to the invention that exerts autoproteolytic function.

In a further preferred embodiment of the present invention the oligopeptide ligand has an amino acid sequence selected from the group consisting of VSIFEW (SEQ ID NO: 6), AVSIEWY (SEQ ID NO: 7), AVSFIWY (SEQ ID NO: 8), VSFIWYK (SEQ ID NO: 9), ASRFWYA (SEQ ID NO: 10), AFYTWYA (SEQ ID NO: 11), AFYRWYK (SEQ ID NO: 12), AFYRWY (SEQ ID NO: 13), AFYRWYA (SEQ ID NO: 14), AVSIFEWY (SEQ ID NO: 15), AVSRNWY (SEQ ID NO: 16), ASRFWY (SEQ ID NO: 17), AFYRWYAA (SEQ ID NO: 18), AFYRWY (SEQ ID NO: 19), ASRFWYAA (SEQ ID NO: 20), AFYRWYAA (SEQ ID NO: 21) and AFYSWYAA (SEQ ID NO: 22).

Within the scope of the present invention oligopeptide ligands may be used with a free N-terminus or with a blocked N-terminus, blocking being achieved e.g. by ac(et)ylation.

Most preferred is an embodiment of the present invention, wherein the derivative of the naturally occurring N$^{pro}$ of CSFV according to SEQ ID NO 5 (since amino acid sequence of this mutant has a sequence motif "EDDIE" (SEQ ID NO: 57) from residue 53 to 57 (instead of "RGDIR" (SEQ ID NO: 58) in the wild type), this mutant (and other mutants comprising this motif) is termed "EDDIE" (SEQ ID NO: 57)-mutant herein) is used in combination with an oligopeptide ligand selected from the group consisting of ASRFWYA (SEQ ID NO: 10), AFYTWYA (SEQ ID NO: 11), AFYRWYK (SEQ ID NO: 12), AFYRWY (SEQ ID NO: 13) and AFYRWYA (SEQ ID NO: 14).

Accordingly, preferred affinity ligands are selected from the group consisting of VSDDWY (SEQ ID NO: 59), VSEDWY (SEQ ID NO: 60), VSIDWY (SEQ ID NO: 61), VSYDWY (SEQ ID NO: 62), VSVDWY (SEQ ID NO: 63), VSWDWY (SEQ ID NO: 64), VSYDWY (SEQ ID NO: 65), VSFDWY (SEQ ID NO: 66), VSDEWY (SEQ ID NO: 67), VSEEWY (SEQ ID NO: 68), VSIEWY (SEQ ID NO: 69), VSYEWY (SEQ ID NO: 70), VSVEWY (SEQ ID NO: 71), VSWEWY (SEQ ID NO: 72), VSYEWY (SEQ ID NO: 73), VSFEWY (SEQ ID NO: 74), DDDDWY (SEQ ID NO: 75), DDEDWY (SEQ ID NO: 76), DDIDWY (SEQ ID NO: 77), DDYDWY (SEQ ID NO: 78), DDVDWY (SEQ ID NO: 79), DDWDWY (SEQ ID NO: 80), DDYDWY (SEQ ID NO: 81), DDFDWY (SEQ ID NO: 82), VSIFWE (SEQ ID NO: 83), FSIFEW (SEQ ID NO: 84), WSIFEW (SEQ ID NO: 85), VSLIWY (SEQ ID NO: 86), VSLIDW (SEQ ID NO: 87), VSLIEW (SEQ ID NO: 88), VSLIWE (SEQ ID NO: 89), FSLEEW (SEQ ID NO: 90), VSDLDW (SEQ ID NO: 91), VSDLEW (SEQ ID NO: 92), VSYIDW (SEQ ID NO: 93), VSYIWE (SEQ ID NO: 94) (all these peptides are binding N$^{pro}$ at pH 5.5), VSIDWY (SEQ ID NO: 95), VSIEWY (SEQ ID NO: 96), VSIWWY (SEQ ID NO: 97), VSIIWY (SEQ ID NO: 98), VSYIWY (SEQ ID NO: 99), VSVIWY (SEQ ID NO: 100), VSFIWY (SEQ ID NO: 101), VSFIWE (SEQ ID NO: 102), VSIFEW (SEQ ID NO: 6), VSIFWE (SEQ ID NO: 103), FSIFEW (SEQ ID NO.: 104), WSIFEW (SEQ ID NO: 105), VSLIWY (SEQ ID NO: 106), VSLIDW (SEQ ID NO: 107), VSLIEW (SEQ ID NO: 108), VSLIWE (SEQ ID NO: 109), FSLIEW (SEQ ID NO: 110), WSLIEW (SEQ ID NO: 111), FSYFEW (SEQ ID NO: 112), FSFYEW (SEQ ID NO: 113), WSFYEW (SEQ ID NO: 114), FSYIEW (SEQ ID NO: 115), WSYIEW (SEQ ID NO: 116) (all these peptides are binding N$^{pro}$ at pH 73), AFYTWYA (SEQ ID NO: 11), AFYRWYK (SEQ ID NO: 12), AFYRWY (SEQ ID NO: 13), AFYRWYA (SEQ ID NO: 14), AFFRWYA (SEQ ID NO: 117), AFGRWYA (SEQ ID NO: 118), AFHRWYA (SEQ ID NO: 119), AFIRWYA (SEQ ID NO: 120), AFLRWYA (SEQ ID NO: 121), AFMRWYA (SEQ ID NO: 202), AFNRWYA (SEQ ID NO: 203), AFPRWYA (SEQ ID NO: 204), AFQRWYA (SEQ ID NO: 205), AFRRWYA (SEQ ID NO: 206), AFSRWYA (SEQ ID NO: 207), AFTRWYA (SEQ ID NO: 122), AFVRWYA (SEQ ID NO: 123), AFYRWYA (SEQ ID NO: 14), AFYFWYA (SEQ ID NO: 124), AFYGWYA (SEQ ID NO: 125), AFYLWYA (SEQ ID NO: 126), AFYMWYA (SEQ ID NO: 127), AFYNWYA (SEQ ID NO: 128), AFYPWYA (SEQ ID NO: 129), AFYTWYA (SEQ ID NO: 11), AFYVWYA (SEQ ID NO: 130), AFYWWYA (SEQ ID NO: 131), AFYYWYA (SEQ ID NO: 132), AKWFRYA (SEQ ID NO: 133), VSRNWY (SEQ ID NO: 134), ASRNWYA (SEQ ID NO: 135), ASRFWYA (SEQ ID NO: 10), FSRNWYA (SEQ ID NO: 136), VFRNWYA (SEQ ID NO: 137), VWRNWYA (SEQ ID NO: 138), VYRNWYA (SEQ ID NO: 139), VSRAWYA (SEQ ID NO: 140), VSRFWYA (SEQ ID NO: 141), VSRWWYA (SEQ ID NO: 142), VSRYWYA (SEQ ID NO: 143), VSRNFYA (SEQ ID NO: 144), VSRNYYA (SEQ ID NO: 145), VSRNWFA (SEQ ID NO: 146), VSRNWWA (SEQ ID NO: 147) (all these peptides have a specifically high affinity to N$^{pro}$ mutants with the EDDIE (SEQ ID NO: 57) motif in amino acid residues 53 to 57), Ac-AFYTWYAK (SEQ ID NO: 148), Ac-AFYRWYKK (SEQ ID NO: 149), Ac-AFYRWYK (SEQ ID NO: 150), Ac-AFYRWYAK (SEQ ID NO: 151), Ac-AFFRWYAK (SEQ ID NO: 152), Ac-AFGRWYAK (SEQ ID NO: 153), Ac-AFHRWYAK (SEQ ID NO: 154), Ac-AFIRWYAK (SEQ ID NO: 155), Ac-AFLRWYAK (SEQ ID NO: 156), Ac-AFMRWYAK (SEQ ID NO: 157), Ac-AFNRWYAK (SEQ ID NO: 158), Ac-AFPRWYAK (SEQ ID NO: 159), Ac-AFQRWYAK (SEQ ID NO: 160), Ac-AFRRWYAK (SEQ ID NO: 161), Ac-AFSRWYAK (SEQ ID NO: 162), Ac-AFTRWYAK (SEQ ID NO: 163), Ac-AFVRWYAK (SEQ ID NO: 164), Ac-AFYRWYAK (SEQ ID NO: 165), Ac-AFYFWYAK (SEQ ID NO: 166), Ac-AFYGWYAK (SEQ ID NO: 167), Ac-AFYLWYAK (SEQ ID NO: 168), Ac-AFYMWYAK (SEQ ID NO: 169), Ac-AFYNWYAK (SEQ ID NO: 170), Ac-AFYPWYAK (SEQ ID NO: 171), Ac-AFYTWYAK (SEQ ID NO: 172), Ac-AFYVWYAK (SEQ ID NO: 173), Ac-AFYWWYAK (SEQ ID NO: 174), Ac-AFYYWYAK (SEQ ID NO: 175), Ac-AKWFRYAK (SEQ ID NO: 176), Ac-VSRNWYK (SEQ ID NO: 177), Ac-ASRNWYAK (SEQ ID NO: 178), Ac-ASRFWYAK (SEQ ID NO: 179), Ac-FSRNWYAK (SEQ ID NO: 180), Ac-VFRNWYAK (SEQ ID NO: 181), Ac-VWRN-WYAK (SEQ ID NO: 182), Ac-VYRNWYAK (SEQ ID NO: 183), Ac-VSRAWYAK (SEQ ID NO: 184), Ac-VSRF-WYAK (SEQ ID NO: 185), Ac-VSRWWYAK (SEQ ID NO: 186), Ac-VSRYWYAK (SEQ ID NO: 187), Ac-VSRNFYAK (SEQ ID NO: 188), Ac-VSRNYYAK (SEQ ID NO: 189), Ac-VSRNWFAK (SEQ ID NO: 190), Ac-VSRNWWAK (SEQ ID NO: 191), YWKA (SEQ ID NO: 192), Ac-YWKAK (SEQ ID NO: 193), YKYA (SEQ ID NO: 194), Ac-YKYAK (SEQ ID NO: 195), YWRA (SEQ ID NO: 196), Ac-YWRAK (SEQ ID NO: 197), ARWY (SEQ ID NO: 198), Ac-ARWYK (SEQ ID NO: 199), YWRA (SEQ ID NO: 200), Ac-YWRAK (SEQ ID NO: 201) (all these peptides have improved immobilisation capabilities to the substrate due to N-terminal acetylation and C-terminal lysination).

For peptide affinity chromatography within the scope of the present invention, any matrix useful for the immobilization of peptide ligands can be used. Preferably Fractogel epoxy (M), from Merck, Darmstadt, Germany) or equally preferred "monolithic chromatography medium" CIM-epoxy is used. The ligands can be immobilized either directly onto the chemically activated backbone of the chromatography matrix, or via a spacer or linker. In the latter case a spacer is coupled to the chromatographic matrix, said spacer is then chemically activated, in order to allow binding of the ligand. Preferably Fractogel epoxy matrices are used in combination with spacers.

In a particularly preferred embodiment of the present invention the spacer is generated by reaction of the chromatographic matrix with diaminodipropylamine (DADPA) and subsequent reaction with succinic anhydride (SA). The resulting terminal carboxy group on the spacer is chemically activated and preferably linked to a terminal amino-group. The ligand is immobilized on the matrix or on the spacer via a reactive group that it comprises. In the case of peptide ligands such reactive groups may be either the amino, carboxy or the sulfhydryl group. Within the present invention anchorage of the peptide on the matrix or the spacer via an amino bond is particularly preferred.

When the binding of the fusion polypeptide to the chromatography system has been accomplished, unbound contaminating components can easily be washed off the column. Such contaminating compounds might for example be host cell polypeptides and nucleic acids, which were occluded into or adsorbed on the inclusion bodies, and remain in the polypeptide solution after solubilization, as well as residual components from an enzymatic cell disruption. After washing only the fusion polypeptide remains bound to the column so that the following steps are conducted in a purified system.

Binding of the fusion polypeptide is established under chaotropic, inactivating conditions. In order to induce refolding, conditions are changed to cosmotropic.

In a preferred embodiment the step of refolding of the fusion polypeptide is performed by the change from chaotropic to cosmotropic conditions via buffer exchange.

Buffers can be alternatively gradually or instantaneously changed to cosmotropic conditions. In one preferred embodiment of the present invention the exchange of chaotropic buffer with cosmotropic buffer is conducted instantaneously, by application of the buffer as a plug. In another equally preferred embodiment of the present invention the exchange of buffers is conducted gradually.

Binding of the fusion polypeptide to the column and/or refolding and cleaving of said fusion polypeptide might be facilitated if the buffer exchange is accompanied by a temperature adjustment. This can, for example, be introduced by a cooling/heating jacket. Therefore, in a preferred embodiment, a cooling/heating jacket is applied for temperature adjustment; more preferably, the buffer is brought to the desired temperature prior to its application. In this way such temperature adjustment is achieved.

Upon change of conditions in the packed bed the fusion polypeptide starts to refold and the part exerting the autoproteolytic function becomes active. As a result, the C-terminally fused polypeptide of interest is cleaved off at a distinct site defined by the specificity of the autoproteolytic part, thereby producing a homogenous N-terminus of the polypeptide of interest. Depending on the time required for refolding of the fusion polypeptide, the velocity of the mobile phase with the cosmotropic buffer is reduced or stopped when all chaotropic buffer is displaced from the packed bed. After refolding is complete, the liberated polypeptide of interest is washed out from the packed bed by further feeding of cosmotropic buffer. The N-terminal autoproteolytic part of the fusion polypeptide as well as un-cleaved fusion polypeptide is eluted by conventional means, e.g. high salt concentration, a pH-change or NaOH, to regenerate the chromatography material. For regeneration the packed bed is washed with a buffer that strips the autoprotease from the adsorbent. These buffers comprise either acidic or alkaline solutions or organic solvents. After re-equilibration with starting buffer/chaotropic buffer the packed bed is ready for the next cycle.

When necessary, because the cleavage rate might not be as high as desired, un-cleaved fusion polypeptide that is washed off the column during the regeneration step can be re-fed into another circle of the chromatography process according to the present invention.

The liberated polypeptide of interest can be obtained optionally via choice of the respective buffers either in a partially or in a completely refolded state. Within the scope of the present invention, the polypeptide of interest in the effluent is either partially or preferably completely refolded. In one embodiment of the present invention, refolding of the autoproteolytic active part of the fusion polypeptide might be complete, while the polypeptide of interest remains partly unfolded. This situation can occur for example when the polypeptide of interest has a very complex conformation, for example a di- or trimerizaton, or comprises a prosthetic group or a cofactor. Such polypeptide of interests might require particular conditions in order to complete refolding. Accordingly in such cases folding may be completed in a separate step, where special conditions, e.g. protonic strength and pH or the complete removal of detergents, which are usually added during refolding, can be generated.

Within the scope of the present invention, the conditions may be changed to any state where the fusion polypeptide stays adsorbed to the column.

The present invention also discloses oligopeptide ligands and derivatives of $N^{pro}$ of CSFV as described hereinabove for use according to the present invention. The present invention also relates to the use of an oligopeptide and a derivative of $N^{pro}$ of CSFV as described hereinabove according to the present invention.

Unless defined otherwise, all technical and scientific terms used herein have the same meaning as commonly understood by one of ordinary skill in the art.

The present invention is described further with reference to the following examples, which are illustrative only and non-

EXAMPLES

Example 1

Production of a Heterologous Polypeptide in Accordance with the Invention, Utilizing Peptide Affinity Chromatography and Different Fusion Polypeptides 1.1. Production of a Heterologous Polypeptide Utilizing $N^{pro}$ Autoprotease of Pestivirus This example describes the production of GFPmut3.1 as a fusion polypeptide of pestivirus autoprotease 6xHis-$N^{pro}$, whereby refolding and cleavage are performed on a peptide affinity matrix.

The GFPmut3.1 used in the fusion construct with $N^{pro}$ in the examples hereafter, is a mutant of GFP which is optimized for production in *E. coli*. GFPmut3.1 carries the following amino acid replacements: S 2 is replaced with R, S 65 with G and S 72 is replaced with A. Position 178 to 415 of the sequence of the entire fusion construct named 6H-sNp-Gmut-3.1-pET30a refer to the sequence of GFPmut3.1.

Construction of the vector 6H-sNp-Gmut3.1-pET30a is described under 1.2.1.1 and 1.2.1.2 below.

Transformation of hostcells is performed as described in 1.2.2 below.

1.1.1 Chromatography Equipment

The chromatography runs in example 1 are performed on an ÄKTA 100 Explorer chromatography system (Amersham Biosciences). The prepared peptide affinity sorbents are packed into HR 5 columns (5 mm i.d., Amersham Biosciences). The gel volume is approximately 1 ml.

1.1.2 Preparation of Oligopeptide Ligands

The oligopeptide ligands used in example 1 are produced in the following way:

Solid Phase Peptide Synthesis is performed on a 433A peptide synthesizer (Applied Biosystems, Vienna, Austria) with 1-hydroxy-1H-benzotriazol/N,N'-dicyclohexylcarbodilmide (HOBtlDCC)-activation of Fmoc-protected amino acids (Bachem, Bubendorf, Switzerland). Peptides are synthesized on a 4-hydroxymethyl-phenoxymethyl-copolystyrene-1% divinylbenzene resin (1-IMP resin, Wang resin). Protecting groups for side chains are tert-butyl (t-Bu) for tyrosine, serine and threonine, OtBu for glutamic acid and aspartic acid, tert-butoxycarbonyl (Boc) for lysine and tryptophane and trityl (Trt) for cystein, histidine, asparagine and glutamine. For the coupling of the first amino acid 4-dimethylaminopyridine (DMAP) is used as a catalyst. After coupling of the first amino acid, a capping step is accomplished by using benzoic anhydride. Deprotection of the Fmoc group is performed with 20% piperidin. Side chain deprotection and cleavage from the resin are carried out by reaction with a cleavage mixture containing 95% trifluoroacetic acid (TFA), 2.5% water and 2.5% triisopropylsilane (TIS). After washing with dichloromethane (DCM) the crude peptide is purified by repeated ether precipitation followed by lyophilization. The peptides are further purified by RP-HPLC on a Luna 15µ C18(2) 250×21.2 mm column (Phenomenex, Torrence, Calif., USA) with P 3500 pumps (Amersham Biosciences, Uppsala, Sweden), using a linear gradient of 5-50% acetonitrile vs. water (0.1% TFA) at 30 ml/min. Purity is confirmed by analytical RP-HPLC with a HP 1090 liquid chromatograph (Hewlett Packard, USA) using a Luna 3µ C18(2) 100× 4.6 mm column (Phenomenex) with a linear gradient of 1% acetonitrile per minute. Homogeneity and identity are verified by matrix assisted laser desorption ionization—time of flight mass spectrometry (ThermoBioanalysis, Hempstead, UK).

1.1.3 Preparation of Affinity Matrix

The affinity matrices used in example 1 are prepared in the following way:

10 g of Fractogel epoxy (M) (Merck, Darmstadt, Germany) is reacted with 50 ml 1 M Diaminodipropylamine (DADPA) for 48 hours at room temperature. After the reaction the gel is washed with a 50 ml 10 mM HCl and 3 times 50 ml water. The gel is resuspended in water, the pH is adjusted to 7.0 by addition of 0.1 M NaOH and 2 g of succinic anhydrid is added. After 30 minutes gentle stirring the pH is adjusted to 7.0 by addition of 10 M NaOH and another 2 g succinic anhydride are added. After another 30 minutes stirring the gel is washed with 50 ml 0.1 M NaOH, 50 ml phosphate buffered saline (PBS), 3 times with 50 ml water and 20% ethanol. After suction drying the gel is stored at 4° C.

1.1.4 Activation of the Carboxy-Group and Immobilization of Peptides:

The affinity matrices according to example 1 are activated in the following way:

1 g of wet Fractogel is modified with a DADPA-SA spacer as described in chapter 1.1.3 and washed 2 times with 5 ml Acetonitrile. Activation is performed with 3 ml 0.1 M Succinimidyl-trichloroethylcarbonate and 0.1 M triethylamine dissolved in acetonitrile for 3 hours. The gel is subsequently washed with acetonitrile and 1 mM HCl. The peptide AFYR-WYA (SEQ ID NO: 14) is dissolved in PBS at a concentration of 3 mg/ml. 5 ml of the peptide solution is rapidly added to the gel and reacted for 24 hours. The peptide VSFIWYK (SEQ ID NO: 9), is dissolved in dimethylformamide (DMF) containing 0.1 M triethylamine. 5 ml of the peptide solution are rapidly added to the gel and reacted for 24 hours. Coupling yield is determined by RP-HPLC of samples before and after coupling.

Immobilization of peptides on CIM-epoxy:

Peptides are dissolved in a 100 mM $Na_2CO_3$ buffer pH 10.0 containing 0.15 M NaCl. The CIM-disks are mounted in a cartridge supplied by the manufacturer and the peptide solution is slowly pumped through the disk using a P1 pump (Amersham Biosciences) in a circulation mode for 48 hours at room temperature. Coupling yield is determined by RP-HPLC of samples before and after coupling. After coupling remaining epoxy groups are blocked with 0.5 M ethanolamine, pH 10.0 for 48 hours.

1.1.5 Expression of the Fusion Polypeptide

Recombinant *E. coli* HMS 174 (DE3) expressing a fusion polypeptide comprising the N-terminal autoprotease $N^{pro}$ with a 6xHis-tag and a C-terminally fused GFPmut3.1 are cultured in a 10 l-fermenter. The fusion polypeptide comprises the following amino acid sequence:

```
SEQ ID NO 23:
  1  MHHHHHHELN  HFELLYKTSK  QKPVGVEEPV  YDTAGRPLFG  NPSEVHPQST  LKLPHDRGRG   60

61  DIRTTLRDLP  RKGDCRSGNH  LGPVSGIYIK  PGPVYYQDYT  GPVYHRAPLE  FFDEAQFCEV  120

121  TKRIGRVTGS  DGKLYHIYVC  VDGCILLKLA  KRGTPRTLKW  IRNFTNCPLW  VTSCSGTMRK  180

181  GEELFTGVVP  ILVELDGDVN  GHKFSVSGEG  EGDATYGKLT  LKFICTTGKL  PVPWPTLVTT  240

241  FGYGVQCFAR  YPDHMKQHDF  FKSAMPEGYV  QERTIFFKDD  GNYKTRAEVK  FEGDTLVNRI  300

301  ELKGIDFKED  GNILGHKLEY  NYNSHNVYIM  ADKQKNGIKV  NFKIRHNIED  GSVQLADHYQ  360

361  QNTPIGDGPV  LLPDNHYLST  QSALSKDPNE  KRDHMVLLEF  VTAAGITHGM  DELYK
```

The bacterial host cell, i.e. the expression strain, is cultivated in accordance with microbiological practice known per se. The strain is generally brought up starting from a single colony on a nutrient medium, but it is also possible to employ cryopreserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). For the cultivation, a small-volume pre-culture of the host strain (inoculated with a single colony or with cell suspension from a cryoculture) is grown, the temperature for this cultivation not generally being critical for the later expression result, so that it is possible routinely to operate at relatively high temperatures (for example 30° C. or 37° C.). The main culture is set up in a larger volume (for example 500 ml), where it is in particular necessary to ensure good aeration (large volume of flask compared with the volume of contents, high speed of rotation). Since it is intended that expression take place in the form of insoluble inclusion bodies, the main culture will in most cases also be carried out at relatively high temperature (for example 30 or 37° C.). Inducible systems are particularly suitable for producing inclusion bodies (for example with trp, lac, tac or phoA promoter). After the late logarithmic phase has been reached (usually at an optical density of 0.5 to 1.0 in shaken flasks), in these cases the inducer substance (for example indoleacrylic acid, isopropyl β-D-thiogalactopyranoside =IPTG) is added and incubation is continued for 1 to 5 hours. During this time, most of the N$^{pro}$ fusion polypeptide is deposited as inclusion bodies in the bacterial cytoplasm. The resulting cells can be harvested and processed further.

On a larger scale, the multistage system consists of a plurality of bioreactors (fermenters), it being preferred to employ defined nutrient media in this case in order to be able to improve the process engineering control of the process. In addition, it is possible greatly to increase biomass and product formation by metering in particular nutrients (fed batch). Otherwise, the process is analogous to the shaken flask. For example, a preliminary stage fermenter and a main stage fermenter are used, the cultivation temperature being chosen similar to that in the shaken flask. The preliminary stage fermenter is inoculated with a so-called inoculum which is generally grown from a single colony or a cryoculture in a shaken flask. Good aeration and a sufficient inducer concentration must also be ensured in the fermenter—and especially in the main stage thereof. The induction phase must, however, in some cases be made distinctly longer compared to the shaken flask. The resulting cells are once again delivered for further processing.

1.1.6 Isolation of Inclusion Bodies

After harvesting, the cells (850 g wet weight) are suspended in 2500 ml of 50 mM Tris/HCl, 5 mM EDTA, 1% Triton X-100, pH 8.0. The chilled suspension is passed through an APV-2000 high pressure homogenizer (Invensys) for three times at 800 bar to disrupt the cells. Between the passages the suspension is chilled on ice and homogenized using an Ultraturrax. The homogenate is centrifuged at low speed (JLA 10.500, 7500 rpm, 30 min) to obtain the inclusion bodies containing the recombinant fusion polypeptide.

1.1.7 Solubilization of Inclusion Bodies

The pellet is suspended in 50 mM Tris/HCl, 5 mM EDTA, 1% Triton X-100, pH 8.0 and centrifuged. This step is repeated. After a H$_2$O-washing step the pellet is suspended in H$_2$O. The obtained inclusion body-suspension is stored at −20° C. for further use. The inclusion body-suspension is diluted 1:5 with 50 mM Tris/HCl, 10 M urea, 50 mM DTT, pH 7.3 at room temperature. Insoluble components are removed by centrifugation. A polypeptide concentration of about 15 mg/ml is obtained. The polypeptide solution is diluted with 50 mM Tris/HCl, 100 mM NaCl, 4 M urea, pH 7.3 to reach a polypeptide concentration of about 2 mg/ml, 1.1.8 Binding of the Fusion Polypeptide to the Chromatographic Column 0.5 ml of the polypeptide solution is applied to a Fractogel-DADPA-SA-VSFIWYK (0.5×5 cm) matrix, whereby preparation and coupling of the respective peptide is conducted as described above in 1.1.2 and 1.1.3. The column is equilibrated with 50 mM Tris/HCl, 100 mM NaCl, 4 M urea, pH 7.3 with a linear flow rate of 50 cm/h. The flow rate is increased to 150 cm/h after sample injection.

1.1.9 Washing Out of Unbound Contaminating Material

Unbound components are washed out with 5 column volumes of equilibration buffer. A buffer exchange to refolding buffer, specifically to 0.5 M Tris/HCl, 2 mM EDTA, 3% glycerol, 5 mM DTT, pH 7.3, is performed with 4.5 column volumes.

1.1.10 Refolding, Cleavage and Elution

After changing the conditions from chaotropic to cosmotropic, the fusion polypeptide is allowed to refold for 25 h on the chromatography resin by stopping the flow. The active autoprotease cleaves off the C-terminally fused GFPmut3.1. The subsequent elution with refolding buffer at a flow rate of 50 cm/h results in purified native GFPmut3.1, as is confirmed by fluorescence measurements and SDS-PAGE.

1.1.11 Regeneration

Regeneration of the chromatography resin is performed with 0.1 M NaOH at a flow rate of 50 cm/h.

1.2 Production of a Heterologous Polypeptide Utilizing a Derivative of N$^{pro}$ Autoprotease of Pestivirus This example describes the production of GFPmut3.1 as a fusion polypeptide of a mutant of pestivirus autoprotease $N^{pro}$: 6xHis-$N^{pro}$ EDDIE (SEQ ID NO: 57), whereby refolding and cleavage are performed on a peptide affinity matrix. Preparation of Oligopeptide Ligands and Affinity Matrix are Performed as Described in Example 1.1., the same chromatography equipment as described in example 1.1 is used.

1.2.1 Construction of the Plasmid:

1.2.1.1 Construction of 7H-Np-Gmut3.1-pET30a Plasmid:

A DNA fragment containing the gene for an N-terminally truncated $N^{pro}$ including a 7-His tag at the N-terminus is amplified by PCR primer pair:

```
T7-pET (SEQ ID NO 24):
5'- GAA ATT AAT ACG ACT CAC TAT AGG -3';

N^pro R-Kpn (SEQ ID NO 25):
5'- ATA CGG TAC CAG AGC AAC TAG TTA CCC ATA ATG-3'
``` from NP6-pET (Sandoz) plasmid and inserted via NdeI and KpnI (Asp718) restriction sites into pET-30a (#69909-3, 2002-2003 catalogue, Novagen, CN Biosciences Inc., Merck KgaA, Darmstadt, Germany). Transformation of the ligation reaction into E. coli DH5alpha (#10643-013, Invitrogen catalogue 2003, Invitrogen Life Technologies Corporation, 1600 Faraday Avenue, PO Box 6482 Carlsbad, Calif. 92008), isolation of plasmid DNA from transformed clones and verification by sequencing results in plasmid 7H-$N^{pro}$-pET30a plasmid. From the plasmid pGFPmut3.1 (#6039-1, catalogue 1999, BD Biosciences Clonetech, 1020 East Meadow Circle, Palo Alto, Calif. 94303-4230, USA) the GFPmut3.1 sequence is also amplified by PCR primer pair:

```
GFP F-Kpn (SEQ ID NO 26):
5'- GAA AGG TAC CAT GCG TAA AGG AGA AG-3'

GFP R-Sal (SEQ ID NO 27):
5'- TAA GTC GAC TTA TTT GTA TAG TTC ATC CAT GCC-3'
``` isolated by gel extraction and cloned via KpnI-SalI restriction sites into the 7H-$N^{pro}$-pET30a construct thus creating the amino acid sequence SGT (serine-glycine-threonine) immediately following the cleavage site. The sequence of construct 7H-Np-Gmut3.1-pET30a is verified as described above.

1.2.1.2 Construction of 6H-sNp-Gmut3.1-pET30a Plasmid:

The DNA sequence for $N^{pro}$-pro-insulin (SEQ ID NO 28):

```
ATGGAACTCAATCATTTCGAACTGCTCTACAAAACTAGCAAGCAAAAAC

CTGTTGGCGTTGAAGAGCCGGTCTACGATACTGCAGGTCGTCCTCTTTT

TGGGAATCCGTCCGAAGTGCACCCCCAGTCAACCCTCAAGCTTCCCCAT

GACCGCGGACGCGGTGACATTCGTACAACGCTGCGCGATCTGCCTCGTA

AAGGCGATTGTCGCTCTGGAAACCACCTAGGTCCGGTGTCGGGCATTTA

CATTAAACCAGGTCCCGTCTATTACCAAGACTACACTGGTCCGGTTTAC

CATCGTGCACCTCTGGAATTCTTTGATGAAGCTCAATTTTGCGAAGTGA

CTAAACGTATTGGCCGTGTAACCGGTTCGGACGGGAAACTGTACCACAT

CTACGTGTGCGTTGATGGCTGTATCCTGCTGAAACTCGCGAAGCGCGGA

ACCCCTCGCACCCTGAAATGGATCCGTAACTTCACTAACTGTCCACTGT

GGGTCACTAGTTGCTTCGTTAACCAACATCTGTGCGGTTCACACCTTGT

GGAAGCCCTGTATCTGGTGTGTGGCGAACGCGGATTCTTTTATACCCCG

AAAACGCGGCGCGAAGCCGAAGATCTTCAGGTTGGTCAAGTGGAACTGG

GCGGAGGTCCGGGAGCCGGGAGCCTGCAACCGCTGGCGCTTGAAGGGTC

GCTGCAAAAACGCGGTATTGTTGAACAGTGCTGTACCTCCATCTGCTCT

CTGTATCAGCTGGAAAACTACTGCAATTAATAA
``` is custom-synthesized and inserted into pUC119 (NCBI # U07650: National Center for Biotechnology Information Plasmid Database, National Library of Medicine, Building 38A, Bethesda, Md. 20894, USA) by Operon Biotechnologies Inc. (1000 Atlantic Avenue, Suite 108 Alameda, Calif. 94501, USA). From this plasmid the $N^{pro}$-pro-insulin sequence, indicated in bold, is amplified by PCR using the following primer pair:

```
6H-N^pro-F-NdeI (SEQ ID NO 29):
5'- CTC TCA TAT GCA TCA CCA TCA TCA TCA CGA ACT
CAA TCA TTT CGA ACT GCT G-3'
and Ins-R-SalI (SEQ ID NO 30):
5'- CTT TCG TCG ACT TAT TAA TTG CAG TAG TTT TC-3'
``` and the resulting fragment is isolated by agarose gel electrophoresis and gel extraction and ligated via the newly created restriction sites for NdeI and SalI (bold letters) into the vector pET30a (#69909-3, 2002-2003 catalog, Novagen, CN Biosciences Inc., Merck KgaA, Darmstadt, Germany) cut at the same restriction sites creating 6H-s$N^{pro}$-Ins-pET30a. 6H-s$^{Npro}$-Ins-pET30a is cut at the SpeI and SalI restriction sites, the larger fragment isolated by gel electrophoresis and extraction, thereby removing the sequence for pro-insulin. To prepare the insert the vector 7HNp-Gmut3.1-pET30a (for construction see 1.2.1.1) is digested by the same enzymes and the excised DNA fragment coding for GFPmut3.1 is isolated by gel extraction. By ligation of this DNA fragment into the prepared vector the construct 6H-sNp-Gmut3.1-pET30a is obtained, coding for a fusion of synthetic $N^{pro}$ with GFPmut3.1. The DNA sequences are controlled as described under 1.2.1.1).

1.2.1.3 Construction of S-Np-Ins-pET30a

From the construct containing the DNA sequence for $N^{pro}$-pro-insulin custom-synthesized and inserted into pUC119 by Operon Biotechnologies Inc the $N^{pro}$-pro-insulin sequence required is amplified by PCR using the following primer pair:

```
N^pro-F-NdeI (SEQ ID NO 31):
5'-CGCGACATATGGAACTCAATCATTTCGAAC-3'
and

Ins-R-SalI (SEQ ID NO 30)
```

The resulting fragment is isolated by agarose gel electrophoresis and gel extraction and ligated via the newly created restriction sites for NdeI and SalI (bold letters) into the vector pET30a, cut at the same restriction sites. The DNA sequence of plasmid s$N^{pro}$-ins-pET30a is controlled as described (see 1.2.1.1).

1.2.1.4 Construction of 6H-EDDIE-sGmut3.1-pET30a plasmid:

From the construct containing the DNA sequence for $N^{pro}$-pro-insulin custom-synthesized and inserted into pUC119 by Operon Biotechnologies Inc the $N^{pro}$-sequence required is amplified by PCR using the following primer pair:

N^pro-F-NdeI (SEQ ID NO 31)
and

N^pro-R-SalI (SEQ ID NO 32):
5'-CGC AGA GAT GTT GGT CGA CGC TGC AAC TAG TG-3' and inserted via the newly created restriction sites for NdeI and SalI (bold letters) into the vector pET30a creating S-Np-6H-pET30a. From S-Np-6H-pET30a the N^pro sequence is amplified by two standard 50 µl PCR reactions: one with 50 pmol N^pro-F-NdeI primer (table 1 below) and 50 pmol reverse mutation primer (3"-), 5 units Taq DNA-polymerase (# GC 002004, 2004 catalog, Genecraft, Treskow Straβe 10, D-48163 Münster, Germany), 1×PCR buffer (# GC 002006, 2004 catalog, Genecraft) and 20 nmol each dNTP mixture (# GC 013004, 2004 catalog, Genecraft); the second with 50 pmol N^pro-R-SalI primer (see table 1 below) and 50 pmol forward mutation primer (5"-), 5 units Taq DNA-polymerase, 1×PCR buffer and 20 nmol each dNTP mixture. PCR reaction takes place in a heated lid thermocycler using the following program: 94° C. for 3 min; 25 cycles: 94° C. for 30 sec, 54° C. for 30 sec, 68° C. for 1 min; final incubation at 68° C. for 7 min. Free primers are removed by QIAquick® PCR Purification Kit (QIAGEN GmbH, Qiagenstrasse 1, D 40724 Hilden, Germany, Cat. Nr. 28106, Qiagen Product Guide 2004) according to the manufacturers recommendations (QIAquick® Spin Handbook July 2002). One-hundredth of both PCRs is combined and amplified in a standard 50 µl PCR reaction with 50 pmol N^pro-F-NdeI primer (SEQ ID NO31) and 50 pmol N^pro-R-SalI primer (SEQ ID NO32), 5 units Taq DNA-polymerase (Genecraft), 1×PCR buffer (Genecraft) and 20 nmol each dNTP mixture (Genecraft) in a heated lid thermocycler using the following program: 94° C. for 3 min; 25 cylces: 94° C. for 30 sec, 54° C. for 30 sec, 68° C. for 1 min; final incubation at 68° C. for 7 min. Free primers are removed by QIAquick PCR Purification Kit (QIAGEN) according to the manufacturers recommendations. The PCR fragments are inserted via the NdeI and SalI restriction sites into vector pET30a. The construct is then used for the next mutational step. This is done in six consecutive steps to introduce the amino acid changes one by one, selecting the respective primers as indicated in table 1 below. The outcoming plasmid of each step is controlled by DNA sequence analysis as described (see 1.2.1.1). The last mutational step (I155T and F158T) is done by a single PCR reaction with the primer pair N^pro-F-NdeI (SEQ ID NO 31)
and 3'_I155T, F158T (SEQ ID NO 33):
5'-GCA ACT AGT GAC CCA CAG TGG ACA GTT AGT GGT GTT ACG GGT CCA TTT CAG G-3' and the resulting PCR product is inserted via the NdeI and SpeI (bold letters, table 1 below) restriction sites into S-Np-6H-pET30a. DNA sequence analysis as described (see 1.2.1.1) verifies the sequence of construct EDDIE-6H-pET30a.

TABLE 1

| | |
|---|---|
| 5'_C112E | SEQ ID NO 34: GCT CAA TTT GAG GAA GTG ACT AAA CG |
| 3'_C112E | SEQ ID NO 35: CGT TTA GTC ACT TCC TCA AAT TGA GC |

TABLE 1-continued

| | |
|---|---|
| 5'_C134E | SEQ ID NO 36: CAT CTA CGT GGA GGT TGA TGG C |
| 3'_C134E | SEQ ID NO 37: GCC ATC AAC CTC CAC GTA GAT G |
| 5'_C138E | SEQ ID NO 38: GTT GAT GGC GAG ATC CTG CTG |
| 3'_C138E | SEQ ID NO 39: CAG CAG GAT CTC GCC ATC AAC |
| 5'_A109T, V114T | SEQ ID NO 40: CTG GAA TTC TTT GAT GAA ACC CAA TTT GAG GAA ACC ACT AAA CGT ATT GG |
| 3'_A109T, V114T | SEQ ID NO 41: CCA ATA CGT TTA GTG GTT TCC TCA AAT TGG GTT TCA TCA AAG AAT TCC AG |
| 5'_R53E, G54D, R57E | SEQ ID NO 42: CAT GAC CGC GGA GAA GAT GAC ATT GAA ACA ACG CTG C |
| 3'_R53E, G54D, R57E | SEQ ID NO 43: GCA GCG TTG TTT CAA TGT TCAC CTT CTC CGC GGT CAT G |
| 5'_L143Q | SEQ ID NO 44: GAT CCT GCT GAA ACA GGC GAA GCG CGG AAC |
| 3'_L143Q | SEQ ID NO 45: GTT CCG CGC TTC GCC TGT TTC AGC AGG ATC |

From EDDIE-6H-pET30a EDDIE (SEQ ID NO: 57) is amplified by PCR using the following primer pair: 6H-$N^{pro}$-F-NdeI, (SEQ ID NO 29) and $N^{pro}$-R-Sal, (SEQ ID NO 32) and the resulting fragment are used to replace $N^{pro}$ via restriction sites for MeI and SpeI (bold letters) in the construct S-Np-Ins-pET30a (see 1.2.1.3) creating 6H-EDDIE-Ins-pET30a. The vector 6H-EDDIE-Ins is digested by SpeI/SalI, the larger fragment isolated by gel electrophoresis and extraction, thereby removing the sequence for pro-insulin. The insert is generated by PCR from a construct containing a synthetic sGFPmut3.1 gene

```
SEQ ID NO 46:
TGCAGCAAAGGCGAAGAACTGTTTACCGGTGTGGTGCCGATTCTGGTGG

AACTGGATGGCGATGTGAACGGTCATAAATTTAGCGTGAGCGGCGAAGG

TGAAGGCGATGCGACCTATGGTAAACTGACCCTGAAATTTATTTGCACC

ACCGGCAAACTGCCGGTGCCGTGGCCGACCCTGGTGACCACCTTTGGTT

ATGGCGTGCAGTGCTTTGCGCGCTATCCGGATCACATGAAACAGCATGA

TTTTTTTAAAAGCGCGATGCCGGAAGGTTATGTGCAGGAACGCACCATT

TTTTTTAAAGATGATGGCAACTATAAAACCCGCGCGGAAGTGAAATTTG

AAGGTGATACCCTGGTGAACCGCATTGAACTGAAAGGCATTGATTTTAA

AGAAGATGGTAACATTCTGGGCCATAAACTGGAATATAACTATAACAGC

CATAACGTGTATATTATGGCGGATAAACAGAAAAACGGTATTAAAGTGA

ACTTTAAAATTCGCCATAACATTGAAGATGGCAGCGTGCAGCTGGCGGA

TCATTATCAGCAGAACACCCCGATTGGTGATGGCCCGGTGCTGCTGCCG

GATAACCATTATCTGAGCACCCAGAGCGCGCTGAGCAAAGATCCGAACG

AAAAACGCGATCACATGGTGCTGCTGGAATTTGTGACCGCGGCGGGTAT

TACGCATGGCATGGATGAACTGTATAAA TAATAA
```

-continued in pUC119 custom-prepared by Operon Biotechnologies Inc with the primer pair sGFP-F-Spe,
(SEQ ID NO 47):
5'-GGA TCC ACT AGT TGC AGC AAA GGC GAA G-3'
and sGFP-R-Sal (SEQ ID NO 48):
5'-CGA GGT CGA CTT ATT ATT TAT ACA GTT CAT C-3'.

The purified PCR product is then digested with SpeI/SalI and ligated into the SpeI/SalI fragment of 6H-EDDIE-Ins, thereby substituting the proinsuline gene by sGmut3.1 to form the construct 6H-EDDIE-sGmut3.1-pET30a. The DNA sequences of each step are controlled as described (see 1.2.1.1).

1.2.2 Transformation:

Electrocompetent cells are prepared from one liter of bacterial culture (grown at 37° C. and 225 rpm to $OD_{600}$=0, 5). The cell suspension is cooled on ice for 15 min (continuous agitation) pelleted (4° C., 2500 g, and 10 min) and the supernatant removed completely. The remaining pellet is re-suspend in one liter of de-ionized water at 4° C., spun down (4° C., 2500 g, 10 min) again and washed 2 times in 50 ml de-ionized water (4° C.) with intermittent centrifuging steps (4° C., 2500 g, 10 min). The pellet is finally washed with 50 ml 10% sterilized glycerol solution (4° C.) pelleted (4° C., 2500 g, 10 min) and re-suspended in 2.5 ml 10% sterilized glycerol solution (4° C.), frozen and stored in 40 µl aliquots at −80° C. One aliquot of electrocompetent cells is thawed on ice, 1 µl of ligation reaction containing 5 ng DNA added and transferred without air bubbles to an electroporation cuvette with 1 mm electrode gap. Electroporation takes place with a BIO-RAD Gene Pulser™ (Bio-Rad Laboratories Inc., 2000 Alfred Nobel Drive, Hercules, Calif. 94547, USA; cat. n. 1652077, Life Science Research Products 1998) including BIO-RAD pulse controller (Bio-Rad Laboratories Inc., 2000 Alfred Nobel Drive, Hercules, Calif. 94547, USA; cat. n. 1652098, Life Science Research Products 1998) set to 1.5 kV, 25 µF, 200 Ohms with a time constant shorter than 4.5 ms. Immediately thereafter 180 µl TY-broth (1.0% w/v Peptone, 0.7% w/v Yeast extract, 0.25% w/v NaCl) is added and the suspension transferred to a sterile 14 ml plastic tube and incubated for 30 min (37° C., 225 rpm). The suspension is then plated on selection medium. After incubation over night at 37° C. colonies are picked, transferred to 2 ml TY-broth and incubated over night at 37° C. and 225 rpm. 1 ml of the overnight culture is used for plasmid preparation by standard methods and the plasmid preparation subjected to restriction analysis and DNA sequencing. After verification by sequence analysis the plasmid is used for further transformation in expression strains by the method described herein.

1.2.3 Expression of the Fusion Polypeptide

Recombinant *E. coli* HMS 174 (DE3) containing a pET30 plasmid expressing a fusion polypeptide with an N-terminal autoprotease 6H-N$^{pro}$EDDIE and a C-terminal GFPmut3.1 with the following amino acid sequence are cultivated in baffled flasks in LB-broth at a total volume of 1.8 l.

Cells are cultivated as described under 1.1.5.

1.2.4 Isolation of Inclusion Bodies

Disruption of the cells is performed enzymatically. Briefly, the cells are suspended in 40 ml of 20 mM Tris/HCl, 5 mM EDTA, 2 mM $MgCl_2$, pH 8.2. 72 mg of lysozyme and 300 U of Benzonase® are added. After incubation for 45 min at RT, 1.3 g NaCl and 0.5 ml Triton X-100 are added. After another 15 min the suspension is centrifuged (Beckman JA 25.50, 10 000 rpm, 15 min, 4° C.) to obtain the inclusion bodies.

1.2.5 Solubilization of Inclusion Bodies

The pellet is washed once in 20 ml of 0.5% deoxycholate, twice in 20 ml of 1 M NaCl, then washed with $H_2O$. The resulting pellet (approximately 2 g wet weight) is suspended in 10 ml of $H_2O$ and stored at −20° C. for further use.

An aliquot of the suspension is diluted 1:5 with 50 mM Tris/HCl, 10 M urea pH 7.3 to dissolve the inclusion bodies. After centrifugation to remove insoluble components the solution is diluted 1:5 with 50 mM Tris/HCl, 100 mM NaCl, 4 M urea, pH 7.3.

1.2.6 Binding of the Fusion Polypeptide 2 ml of the solution with an approximate polypeptide concentration of 2 mg/ml are applied onto a peptide affinity matrix as described above. Briefly, a Fractogel-DADPA-SA-AFYRWYA (0.5 inner diameter×5 cm) is equilibrated with 50 mM Tris/HCl, 100 mM NaCl, 4 M Urea, pH 7.3. 2 ml of the sample are injected at a flow rate of 25 cm/h.

1.2.7 Washing Out of Unbound Contaminating Material

Unbound components are washed out with 5 column volumes of equilibration buffer at a flow rate of 150 cm/h. Refolding is induced by a buffer exchange with 4.5 column volumes of 200 mM Tris/HCl, 2 mM EDTA, 10% Glycerol, pH 7.3.

1.2.8 Refolding, Cleavage and Elution

The bound fusion polypeptide is allowed to refold for 25 h by stopping the flow. Upon the refolding the bound autoprotease cleaves at its specific site and releases the fusion partner GFPmut3.1. Then the fusion polypeptide is washed out by the a 200 mM Tris/HCl, 2 mM EDTA, 10% Glycerol, pH 7.3 buffer using a flow rate of 150 cm/h. 1 ml fractions are collected and analyzed for UV absorbance at 280 nm and fluorescence at an excitation of 488 nm and emission of 520 nm. Fractions containing the fusion partner GFPmut3.1 are further analyzed by SDS-PAGE for purified GFPmut3.1.

1.2.9 Regeneration

After elution of the cleaved off polypeptide of interest regeneration of the column is performed with 5 column volumes of 0.1 M NaOH at a flow rate of 150 cm/h.

Example 2

Production of a Heterologous Polypeptide in Accordance with the Invention, Utilizing Immobilized Metal Ion Affinity Chromatography This example describes the production of GFPmut3.1 as a fusion polypeptide of a mutant of pestivirus autoprotease N$^{pro}$: 6xHis-N$^{pro}$EDDIE, whereby refolding and cleavage are performed on an immobilized metal ion affinity matrix.

```
SEQ ID NO 49:
  1  MHHHHHHELN HFELLYKTSK QKPVGVEEPV YDTAGRPLFG NPSEVHPQST LKLPHDRGED    60
 61  DIETTLRDLP RKGDCRSGNH LGPVSGIYIK PGPVYYQDYT GPVYHRAPLE FFDETQFEET   120
121  TKRIGRVTGS DGKLYHIYVE VDGEILLKQA KRGTPRTLKW TRNTTNCPLW VTSCSKGEEL   180
181  FTGVVPILVE LDGDVNGHKF SVSGEGEGDA TYGKLTLKFI CTTGKLPVPW PTLVTTFGYG   240
241  VQCFARYPDH MKQHDFFKSA MPEGYVQERT IFFKDDGNYK TRAEVKFEGD TLVNRIELKG   300
301  IDFKEDGNIL GHKLEYNYNS HNVYIMADKQ KNGIKVNFKI RHNIEDGSVQ LADHYQQNTP   360
361  IGDGPVLLPD NHYLSTQSAL SKDPNEKRDH MVLLEFVTAA GITHGMDELY K
```

The His-tag is introduced into the fusion polypeptide in order to be able to use the same construct in both IMAC and peptide affinity chromatography so that both methods can be directly compared. The tag is not required for the interaction of the fusion polypeptide with the oligopeptide ligand during affinity chromatography.

Preparation and solubilization of inclusion bodies is performed as described in example 1.2.4 and 1.2.5.

2.1 Preparation of Chromatographic Column Binding of the Fusion Polypeptide to the Chromatographic Column Chelating Sepharose Fast flow (Amersham Biosciences) is packed into the column to a bed dimension of 0.5 inner diameter×5 cm and storage solution is washed out with water. In a next step the metal ion $Ni^{2+}$ is loaded onto the column. About two thirds of the total column volume of 100 mM $NiCl_2$ or $NiSO_4$ are applied. Unbound $Ni^{2+}$ ions are washed out. After equilibration of the column with 50 mM Tris, 100 mM NaCl, 4 M urea, pH 7.3, 0.5 ml of the polypeptide solution with a concentration of about 2 mg/ml is applied onto the column. The loading flow rate is 50 cm/h.

2.2 Washing Out of Unbound Contaminating Material

After washing out unbound sample components with 5 column volumes of equilibration buffer, a buffer exchange to 500 mM Tris/Acetate, 0.25 M sucrose, 1 mM DTT, pH 7.3 is performed.

2.3 Refolding, Cleavage and Elution

After 4.5 column volumes the flow is stopped to allow the fusion polypeptide to refold and upon refolding the autoprotease cleaves off the fusion partner. Elution of the polypeptide of interest is performed by activating the flow again at a velocity of 150 cm/h using 1 ml of 500 mM Tris/Acetate, 0.25 M sucrose, 1 mM DTT, pH 7.3buffer. Fractions are collected and analyzed by fluorescence measurements and SDS-PAGE.

2.4 Regeneration

Regeneration of the chromatography resin is carried out with 50 mM acetate, 6 M guanidinium chloride, pH 3.5 at a flow rate of 50 cm/h.

Example 3

On Column Cleavage of $N^{pro}$EDDIE-sSPA-D

This example describes the production of staphylococcal Protein A domain D by expression as a fusion polypeptide of a mutant of pestivirus autoprotease Npro: $N^{pro}$EDDIE, whereby refolding and cleavage are performed on a peptide affinity matrix. A fusion protein comprising the autoprotease $N^{pro}$EDDIE and the C-terminally fused Protein A domain D (sSPA-D) referred to as $N^{pro}$EDDIE-sSPA-D are prepared as follows:

Recombinant *E. coli* HMS 174 (DE3) containing a pET30 plasmid expressing the fusion polypeptide with the following amino acid sequence are cultivated in a 10 l fermenter as described in 1.1.5. Amino acids 1 to 168 of the entire fusion construct refer to the sequence of NproEDDIE whereas amino acids 169 to 229 refer to the sequence of sSPA-D.

Isolation and solubilization of inclusion bodies takes place as described in example 1.1.

Binding of the fusion polypeptide to the chromatographic column Fractogel-DADPA-IT-peptide (0.5×5 cm) matrix, whereby selection and coupling of the respective peptide is conducted as described above, is equilibrated with 50 mM Tris/HCl, 100 mM NaCl, 4 M urea, pH 7.3 with a linear flow rate of 150 cm/h. 1 ml of the polypeptide solution is applied at a linear flow velocity of 50 cm/h. The flow rate is increased to 150 cm/h after sample injection.

Washing Out of Unbound Contaminating Material

Unbound components are washed out with 5 column volumes of equilibration buffer. A buffer exchange to refolding buffer, specifically to 1 M Tris/HCl, 2 mM EDTA, 0.25 M sucrose, 10 mM □-monothioglycerol, pH 7.3, is performed with 6 column volumes.

Refolding, Cleavage and Elution

After changing the conditions from chaotropic to cosmotropic, the fusion polypeptide is allowed to refold for 25 h on the chromatography resin by stopping the flow. The active autoprotease cleaves off the C-terminally fused sSPA-D. The subsequent elution with refolding buffer results in native sSPA-D. Regeneration of the matrices is performed with 10 CV of 0.2 M NaOH at 150 cm/h.

Example 4

On Column Refolding and Cleavage of 6His-$N^{pro}$EDDIE-GFPmut3.1

This example describes the production of native GFPmut-3.1 by expression of a 6His-$N^{pro}$EDDIE-GFPmut3.1 fusion polypeptide, refolding and cleavage on an affinity matrix referred to as Actigel-polyKW. Chromatography conditions are the same as described above.

Example 5

On Column Cleavage of $N^{pro}$EDDIE-sSPA-D

This example describes the production of native sSPA-D by expression of a $N^{pro}$EDDIE-sSPA-D fusion polypeptide, refolding and cleavage on an affinity matrix referred to as Actigel-polyKY. Chromatography conditions are the same as described above.

Example 6

On-Column Refolding Using Cation-Exchange Chromatography

Crude $N^{pro}$-6His (SEQ ID NO: 4)
((1)MELNHFELLYKTSKQKPVGVEEPVYD-TAGRPLFGNPSEVHPQSTLKLPDRGRGDIRTTLR DLPRKGDCRSGNHLGP VSGIYIKPGPVYYQDYTG-PVYHRAPLEFFDETQFEETTKRIGRVTGS DGKLY-HIYVEVDGEILLKLAKRGTPRTLKWTR

```
                                                      (SEQ ID NO: 208)
          1          11         21         31         41         51
          |          |          |          |          |          |
  1   MELNHFELLY KTSKQKPVGV EEPVYDTAGR PLFGNPSEVH PQSTLKLPHD RGEDDIETTL   60
 61   RDLPRKGDCR SGNHLGPVSG IYIKPGPVYY QDYTGPVYHR APLEFFDETQ FEETTKRIGR  120
121   VTGSDGKLYH IYVEVDGEIL LKQAKRGTPR TLKWTRNTTN CPLWVTSCAD AQQNKFNKDQ  180
181   QSAFYEILNM PNLNEEQRNG FIQSLKDDPS QSTNVLGEAK KLNESQAPK
```

NTTNCPLWVISC-(168)) inclusion body extracts were resuspended in 8 M urea, 50 mM Na-phosphate pH 7.0. The final protein concentration was 0.5 mg/ml. 2 ml were loaded onto a HiTrap SP Sepharose FF column (2.5×0.7 cm i.d.; column volume 1 ml; GE Healthcare) at a linear velocity of 50 cm/h previously equilibrated with the same buffer as described above. The column was then buffer-exchanged into a buffer containing 50 mM Na-phosphate pH 7, 2 mM EDTA, 5% glycerol, 10 mM α-monothioglycerol (MTG). The protein was allowed to refold for 1 hour at room temperature. Elution of refolded and cleaved proteins was carried out by further application of refolding buffer. Regeneration was performed with a buffer containing 2 M NaCl, 50 mM Na-phosphate pH 7. Refolding of the fusion protein (6 His) was monitored by SDS-PAGE analysis.

The invention claimed is:

1. A method for the production of a heterologous polypeptide of interest with a homogenous N-terminus, using a fusion polypeptide comprising the heterologous polypeptide of interest and N-terminally thereto a polypeptide exhibiting autoproteolytic function, said method comprising the steps of a) binding of the fusion polypeptide in a soluble, autoproteolytically inactive form by an affinity chromatography system, b) refolding of the fusion polypeptide, thereby activating the autoproteolytic function of the fusion polypeptide and causing cleavage of the heterologous polypeptide of interest, and c) subsequently eluting the heterologous polypeptide of interest, wherein said steps are conducted on one affinity chromatography system wherein said method utilizes an oligopolypeptide ligand selected from the group consisting of:

```
VSDDWY,     (SEQ ID NO: 59)
VSEDWY,     (SEQ ID NO: 60)
VSIDWY,     (SEQ ID NO: 61)
VSYDWY,     (SEQ ID NO: 62)
VSVDWY,     (SEQ ID NO: 63)
VSWDWY,     (SEQ ID NO: 64)
VSYDWY,     (SEQ ID NO: 65)
VSFDWY,     (SEQ ID NO: 66)
VSDEWY,     (SEQ ID NO: 67)
VSEEWY,     (SEQ ID NO: 68)
VSIEWY,     (SEQ ID NO: 69)
VSYEWY,     (SEQ ID NO: 70)
VSVEWY,     (SEQ ID NO: 71)
VSWEWY,     (SEQ ID NO: 72)
VSYEWY,     (SEQ ID NO: 73)
VSFEWY,     (SEQ ID NO: 74)
DDDDWY,     (SEQ ID NO: 75)
DDEDWY,     (SEQ ID NO: 76)
DDIDWY,     (SEQ ID NO: 77)
DDYDWY,     (SEQ ID NO: 78)
DDVDWY,     (SEQ ID NO: 79)
DDWDWY,     (SEQ ID NO: 80)
DDYDWY,     (SEQ ID NO: 81)
DDFDWY,     (SEQ ID NO: 82)
VSIFWE,     (SEQ ID NO: 83)
FSIFEW,     (SEQ ID NO: 84)
WSIFEW,     (SEQ ID NO: 85)
VSLIWY,     (SEQ ID NO: 86)
VSLIDW,     (SEQ ID NO: 87)
VSLIEW,     (SEQ ID NO: 88)
VSLIWE,     (SEQ ID NO: 89)
FSLEEW,     (SEQ ID NO: 90)
VSDLDW,     (SEQ ID NO: 91)
VSDLEW,     (SEQ ID NO: 92)
VSYIDW,     (SEQ ID NO: 93)
VSYIWE,     (SEQ ID NO: 94)
VSIDWY,     (SEQ ID NO: 95)
VSIEWY,     (SEQ ID NO: 96)
VSIWWY,     (SEQ ID NO: 97)
VSIIWY,     (SEQ ID NO: 98)
VSYIWY,     (SEQ ID NO: 99)
VSVIWY,     (SEQ ID NO: 100)
VSFIWY,     (SEQ ID NO: 101)
VSFIWE,     (SEQ ID NO: 102)
FSLIEW,     (SEQ ID NO: 110)
WSLIEW,     (SEQ ID NO: 111)
FSYFEW,     (SEQ ID NO: 112)
FSFYEW,     (SEQ ID NO: 113)
WSFYEW,     (SEQ ID NO: 114)
FSYIEW,     (SEQ ID NO: 115)
WSYIEW,     (SEQ ID NO: 116)
AFYTWYA,    (SEQ ID NO: 11)
AFFRWYA,    (SEQ ID NO: 117)
AFGRWYA,    (SEQ ID NO: 118)
AFHRWYA,    (SEQ ID NO: 119)
AFIRWYA,    (SEQ ID NO: 120)
AFLRWYA,    (SEQ ID NO: 121)
```

| | | | | |
|---|---|---|---|---|
| AFMRWYA, | (SEQ ID NO: 202) | | Ac-AFIRWYAK, | (SEQ ID NO: 155) |
| AFNRWYA, | (SEQ ID NO: 203) | | Ac-AFLRWYAK, | (SEQ ID NO: 156) |
| AFPRWYA, | (SEQ ID NO: 204) | | Ac-AFMRWYAK, | (SEQ ID NO: 157) |
| AFQRWYA, | (SEQ ID NO: 205) | | Ac-AFNRWYAK, | (SEQ ID NO: 158) |
| AFRRWYA, | (SEQ ID NO: 206) | | Ac-AFPRWYAK, | (SEQ ID NO: 159) |
| AFSRWYA, | (SEQ ID NO: 207) | | Ac-AFQRWYAK, | (SEQ ID NO: 160) |
| AFTRWYA, | (SEQ ID NO: 122) | | Ac-AFRRWYAK, | (SEQ ID NO: 161) |
| AFVRWYA, | (SEQ ID NO: 123) | | Ac-AFSRWYAK, | (SEQ ID NO: 162) |
| AFYRWYA, | (SEQ ID NO: 14) | | Ac-AFTRWYAK, | (SEQ ID NO: 163) |
| AFYFWYA, | (SEQ ID NO: 124) | | Ac-AFVRWYAK, | (SEQ ID NO: 164) |
| AFYGWYA, | (SEQ ID NO: 125) | | Ac-AFYRWYAK, | (SEQ ID NO: 165) |
| AFYLWYA, | (SEQ ID NO: 126) | | Ac-AFYFWYAK, | (SEQ ID NO: 166) |
| AFYMWYA, | (SEQ ID NO: 127) | | Ac-AFYGWYAK, | (SEQ ID NO: 167) |
| AFYNWYA, | (SEQ ID NO: 128) | | Ac-AFYLWYAK, | (SEQ ID NO: 168) |
| AFYPWYA, | (SEQ ID NO: 129) | | Ac-AFYMWYAK, | (SEQ ID NO: 169) |
| AFYVWYA, | (SEQ ID NO: 130) | | Ac-AFYNWYAK, | (SEQ ID NO: 170) |
| AFYWWYA, | (SEQ ID NO: 131) | | Ac-AFYPWYAK, | (SEQ ID NO: 171) |
| AFYYWYA, | (SEQ ID NO: 132) | | Ac-AFYTWYAK, | (SEQ ID NO: 172) |
| AKWFRYA, | (SEQ ID NO: 133) | | Ac-AFYVWYAK, | (SEQ ID NO: 173) |
| VSRNWY, | (SEQ ID NO: 134) | | Ac-AFYWWYAK, | (SEQ ID NO: 174) |
| ASRNWYA, | (SEQ ID NO: 135) | | Ac-AFYYWYAK, | (SEQ ID NO: 175) |
| FSRNWYA, | (SEQ ID NO: 136) | | Ac-AKWFRYAK, | (SEQ ID NO: 176) |
| VFRNWYA, | (SEQ ID NO: 137) | | Ac-VSRNWYK, | (SEQ ID NO: 177) |
| VWRNWYA, | (SEQ ID NO: 138) | | Ac-ASRNWYAK, | (SEQ ID NO: 178) |
| VYRNWYA, | (SEQ ID NO: 139) | | Ac-ASRFWYAK, | (SEQ ID NO: 179) |
| VSRAWYA, | (SEQ ID NO: 140) | | Ac-FSRNWYAK, | (SEQ ID NO: 180) |
| VSRFWYA, | (SEQ ID NO: 141) | | Ac-VFRNWYAK, | (SEQ ID NO: 181) |
| VSRWWYA, | (SEQ ID NO: 142) | | Ac-VWRNWYAK, | (SEQ ID NO: 182) |
| VSRYWYA, | (SEQ ID NO: 143) | | Ac-VYRNWYAK, | (SEQ ID NO: 183) |
| VSRNFYA, | (SEQ ID NO: 144) | | Ac-VSRAWYAK, | (SEQ ID NO: 184) |
| VSRNYYA, | (SEQ ID NO: 145) | | Ac-VSRFWYAK, | (SEQ ID NO: 185) |
| VSRNWFA, | (SEQ ID NO: 146) | | Ac-VSRWWYAK, | (SEQ ID NO: 186) |
| VSRNWWA, | (SEQ ID NO: 147) | | Ac-VSRYWYAK, | (SEQ ID NO: 187) |
| Ac-AFYTWYAK, | (SEQ ID NO: 148) | | Ac-VSRNFYAK, | (SEQ ID NO: 188) |
| Ac-AFYRWYKK, | (SEQ ID NO: 149) | | Ac-VSRNYYAK, | (SEQ ID NO: 189) |
| Ac-AFYRWYK, | (SEQ ID NO: 150) | | Ac-VSRNWFAK, | (SEQ ID NO: 190) |
| Ac-AFYRWYAK, | (SEQ ID NO: 151) | | Ac-VSRNWWAK, | (SEQ ID NO: 191) |
| Ac-AFFRWYAK, | (SEQ ID NO: 152) | | YWKA, | (SEQ ID NO: 192) |
| Ac-AFGRWYAK, | (SEQ ID NO: 153) | | Ac-YWKAK, | (SEQ ID NO: 193) |
| Ac-AFHRWYAK, | (SEQ ID NO: 154) | | YKYA, | (SEQ ID NO: 194) |

| | |
|---|---|
| Ac-YKYAK, | (SEQ ID NO: 195) |
| ARWY, | (SEQ ID NO: 198) |
| Ac-ARWYK, | (SEQ ID NO: 199) |
| YWRA, and | (SEQ ID NO: 200) |
| Ac-YWRAK | (SEQ ID NO: 201) | which selectively binds to the part of the fusion polypeptide exerting autoproteolytic function under chaotropic conditions.

2. The method according to claim 1, wherein the fusion polypeptide is provided by recombinant expression in a bacterial host cell in the form of inclusion bodies, utilizing a host cell that is transformed with an expression vector comprising a nucleic acid molecule which codes for the fusion polypeptide.

3. The method according to claim 1, wherein the polypeptide exhibiting autoproteolytic function is an autoprotease.

4. The method according to claim 3, wherein the autoprotease is Npro of a pestivirus.

5. The method according to claim 4, wherein the pestivirus is selected from the group consisting of CSFV, BDV and BVDV.

6. The method according to claim 5, wherein the autoprotease is Npro of CSFV and has the following amino acid sequence:

SEQ ID NO 1:
(1)-MELNHFELLYKTSKQKPVGVEEPVYDTAGRPLFGNPSEVHPQSTL

KLPHDRGRGDIRTTLRDLPRKGDCRSGNHLGPVSGIYIKPGPVYYQDYT

GPVYHRAPLEFFDEAQFCEVTKRIGRVTGSDGKLYHIYVCVDGCILLKL

AKRGTPRTLKWIRNFTNCPLWVTSC-(168).

7. The method according to claim 5, wherein the autoprotease is a derivative of Npro of CSFV and has the following amino acid sequence:

SEQ ID NO 2:
(1)-MELNHFELLYKTSKQKPVGVEEPVYDTAGRPLFGNPSEVHPQSTL

KLPHDRGRGDIRTTLRDLPRKGDCRSGNHLGPVSGIYIKPGPVYYQDYT

GPVYHRAPLEFFDEAQFEEVTKRIGRVTGSDGKLYHIYVEVDGEILLKL

AKRGTPRTLKWIRN FTNCPLWVTSC-(168).

8. The method according to claim 5, wherein the autoprotease is a derivative of Npro of CSFV and has the following amino acid sequence:

SEQ ID NO 3:
(1)-MELNHFELLYKTSKQKPVGVEEPVYDTAGRPLFGNPSEVHPQSTL

KLPHDRGEDDIETTLRDLPRKGDCRSGNHLGPVSGIYIKPGPVYYQDYT

GPVYHRAPLEFFDEAQFEEVTKRIGRVTGSDGKLYHIYVEVDGEILLKQ

AKRGTPRTLKWIRNFTNCPLWVTSC-(168).

9. The method according to claim 5, wherein the autoprotease is a derivative of Npro of CSFV and has the following amino acid sequence:

SEQ ID NO 4:
(1)-MELNHFELLYKTSKQKPVGVEEPVYDTAGRPLFGNPSEVHPQSTL

KLPHDRGRGDIRTTLRDLPRKGDCRSGNHLGPVSGIYIKPGPVYYQDYT

GPVYHRAPLEFFDETQFEETTKRIGRVTGSDGKLYHIYVEVDGEILLKL

AKRGTPRTLKWTRNTTNCPLWVTSC-(168).

10. The method according to claim 5, wherein the autoprotease is a derivative of Npro of CSFV and has the following amino acid sequence:

SEQ ID NO 5:
(1)-MELNHFELLYKTSKQKPVGVEEPVYDTAGRPLFGNPSEVHPQSTL

KLPHDRGEDDIETTLRDLPRKGDCRSGNHLGPVSGIYIKPGPVYYQDYT

GPVYHRAPLEFFDETQFEETTKRIGRVTGSDGKLYHIYVEVDGEILLKQ

AKRGTPRTLKWTRNTTNCPLWVTSC-(168).

11. The method according to claim 1, wherein the affinity chromatography system is selected from the group consisting of immobilized metal ion chromatography (IMAC), cation exchange chromatography, anion exchange chromatography, cellulose binding domain chromatography and peptide affinity chromatography.

12. The method according to claim 11, wherein the affinity chromatography system is immobilized metal ion chromatography and wherein the fusion polypeptide comprises a metal chelate affinity tag.

13. The method according to claim 12, wherein the metal chelate affinity tag is polyhistidine.

14. The method according to claim 11, wherein the affinity chromatography system is cation exchange chromatography and wherein the fusion polypeptide comprises a polycationic affinity tag.

15. The method according to claim 14, wherein the polycationic affinity tag is selected from polyarginine and polylysine.

16. The method according to claim 11, wherein the affinity chromatography system is anion exchange chromatography and wherein the fusion polypeptide comprises a polyanionic tag.

17. The method according to claim 16, wherein the polyanionic tag is polyasparagine.

18. The method according to claim 1, wherein the step of refolding the fusion polypeptide is performed by the change from chaotropic to cosmotropic conditions via buffer exchange.

\* \* \* \* \*